United States Patent
Senter et al.

(10) Patent No.: US 7,091,186 B2
(45) Date of Patent: Aug. 15, 2006

(54) P-AMIDOBENZYLETHERS IN DRUG DELIVERY AGENTS

(75) Inventors: Peter D. Senter, Seattle, WA (US); Brian E. Toki, Lynnwood, WA (US)

(73) Assignee: Seattle Genetics, Inc., Bothell, WA (US)

( * ) Notice: Subject to any disclaimer, the term of this patent is extended or adjusted under 35 U.S.C. 154(b) by 669 days.

(21) Appl. No.: 09/963,103

(22) Filed: Sep. 24, 2001

(65) Prior Publication Data

US 2003/0096743 A1 May 22, 2003

(51) Int. Cl.
C07K 5/06 (2006.01)
(52) U.S. Cl. .................. 514/19; 530/331; 514/18; 514/717
(58) Field of Classification Search ................ 530/330, 530/331; 514/18, 19, 717
See application file for complete search history.

(56) References Cited

U.S. PATENT DOCUMENTS

| | | | | |
|---|---|---|---|---|
| 4,457,940 | A | * | 7/1984 | Katsuda et al. ............. 514/411 |
| 4,661,050 | A | * | 4/1987 | Deminski ................... 417/454 |
| 5,026,628 | A | * | 6/1991 | Begley et al. .............. 430/382 |
| 5,274,886 | A | * | 1/1994 | Oetiker ..................... 24/20 TT |
| 5,668,117 | A | * | 9/1997 | Shapiro ...................... 514/55 |
| 6,413,507 | B1 | | 7/2002 | Bentley et al. |
| 6,429,207 | B1 | | 8/2002 | Van Wagenen et al. |
| 6,613,879 | B1 | * | 9/2003 | Firestone et al. ........... 530/330 |
| 6,759,509 | B1 | * | 7/2004 | King et al. ................. 530/330 |
| 2003/0130189 | A1 | * | 7/2003 | Senter et al. ................ 514/12 |
| 2004/0121940 | A1 | * | 6/2004 | De Groot et al. ............... 514/2 |

FOREIGN PATENT DOCUMENTS

EP 0 624 377 A2 11/1994

OTHER PUBLICATIONS de Groot et al., 2002, "Design, Synthesis, and Biological Evaluation of a Dual Tumor-Specific Motive Containing Integrin-targeted Plasmin-cleavable Doxorubicin Prodrug," *Molecular Cancer Therapeutics* 1:901-911.
de Groot et al., 2001, "Elongated Multiple Electronic Cascade and Cyclization Spacer Systems in Activatible Anticancer Prodrugs for Enhanced Drug Release," *J. Org. Chem.* 66(26):8815-8830.
Dubowchik et al., 1997, "Monomethoxytrityl (MMT) as a Versatile Amino Acid Protecting Group for Complex Prodrugs of Anticancer Compounds Sensitive to Strong Acids, Bases and Nucleophiles", *Tetrahedron Letters* 38(30):5257-5260.
Dubowchik et al., 2002, "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity", *Bioconjugate Chem.* 13:855-869.
Carl et al., 1981, "A novel connector linkage applicable in prodrug design", J. Med. Chem. 24:479-480.
Carl et al., 1980, "Protease-activated 'prodrugs' for cancer chemotherapy", Proc. Natl. Acad. Sci. USA 77:2224-2228.
Chakravarty et al., 1983, "Plasmin-activated prodrugs for cancer chemotherapy. 1. Synthesis and biological activity of peptidylacivicin and peptidylphenylenediamine mustard", J. Med. Chem. 26:633-638.
Chakravarty et al., 1983, "Plasmin-activated prodrugs for cancer chemotherapy. 2. Synthesis and biological activity of peptidyl derivatives of doxorubicin", J. Med. Chem. 26:638-644.
Davidson et al., 1997, "The inhibition of matrix metalloproteinase enzymes", Chemistry & Industry, Apr. 7, 1997, p. 258-261.
de Groot et al., 2000, "Synthesis and biological evaluation of 2'-carbamate-linked and 2'-carbonate-linked prodrugs of paclitaxel: selective activation by the tumor-associated protease plasmin", J. Med. Chem. 43:3093-3102.
de Groot et al., 1999, "Synthesis and biological evaluation of novel prodrugs of anthracyclines for selective activation by the tumor-associated protease plasmin", J. Med. Chem. 42:5277-5283.
Demchik and Sloane, 1999, "Cell-surface proteases in cancer", in: *Proteases : New Perspectives*, Turk, ed., Birkhäuser Verlag, Basel, Switzerland, pp. 109-124.
Denmeade et al., 1998, "Enzymatic activation of a doxorubicin-peptide prodrug by prostate-specific antigen", Cancer Res. 58:2537-2540.
Dubowchik and Walker, 1999, "Receptor-mediated and enzyme-dependent targeting of cytotoxic anticancer drugs", Pharmacol. Therapeut. 83:67-123.
Dubowchik and Firestone, 1998, "Cathepsin B-sensitive dipeptide prodrugs. 1. A model study of structural requirements for efficient release of doxorubicin", Bioorg. Med. Chem. Lett. 8:3341-3346.

(Continued)

*Primary Examiner*—David Lukton
(74) *Attorney, Agent, or Firm*—Jones Day

(57) ABSTRACT

Compounds of the formulae

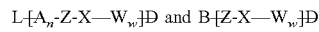

wherein: D is a drug moiety; L is a ligand; B is a blocking group; A is an optional acyl unit; Z is an amino acid or a peptide residue; X is an aminobenzyl ether self-immolative spacer group; W is an optional second self-immolative group; n is an integer of 0 or 1; and w is an integer of 0 or 1, and compositions of said compounds with pharmaceutically acceptable carrier, diluent and/or excipient, and methods of delivery the drug D via the compounds.

38 Claims, 6 Drawing Sheets

OTHER PUBLICATIONS

Dubowchik et al., 1998, "Cathepsin B-sensitive dipeptide prodrugs. 2. Models of anticancer drugs paclitaxel (Taxol®), mitomycin C and doxorubicin", Bioorg. Med. Chem. Lett. 8:3347-3352.

Greenwald et al., 1999, "Drug delivery systems employing 1,4- or 1,6-elimination: poly(ethylene glycol) prodrugs of amine-containing compounds", J. Med. Chem. 42:3657-3667.

Harada et al., 2000, "Determinants for the drug release from T-0128, camptothecin analogue-carboxymethyl dextran conjugate", J. Controlled Release 69:399-412.

Koblinski et al., 2000, "Unraveling the role of proteases in cancer", Clin. Chim. Acta 291:113-135.

Loadman et al., 1999, "Pharmacokinetics of PK1 and doxorubicin in experimental colon tumor models with differing responses to PK1", Clin. Cancer Res. 5:3682-3688.

Mai et al., 2000, "Cell surface complex of cathepsin B/annexin II tetramer in malignant progression", Biochim. Biophys. Acta 1477:215-230.

Niculescu-Duvaz et al., 1999, "Self-immolative anthracycline prodrugs for suicide gene therapy", J. Med. Chem. 42:2485-2489.

Putnam et al., 1996, "Intracellularly biorecognizable derivatives of 5-fluorouracil", Biochem. Pharmacol. 52:957-962.

Senter et al., 1996, "The role of rat serum carboxylesterase in the activation of paclitaxel and camptothecin prodrugs", Cancer Res. 56:1471-1474.

Teicher and Sartorelli, 1980, "Nitrobenzyl halides and carbarnates as prototype bioreductive alkylating agents", J. Med. Chem. 23:955-960.

Ueda et al., 1995, "Novel, water-soluble phosphate derivatives of 2'-ethoxycarbonylpaclitaxel as potential prodrugs of paclitaxel: synthesis and antitumor evaluation", Bioorg. Med. Chem. Lett. 5:247-252.

Wakselman, 1983, "1,4- and 1,6-eliminations from hydroxy- and amino-substituted benzyl systems: chemical and biochemical applications", Noveau J. de Chimie 7:439-447.

International Search Report dated Jul. 27, 2004, issued in connection with International application No. PCT/US02/30282.

Ghosh et al., 2000, "Nature of linkage between the cationic headgroup and cholesteryl skeleton controls gene transfection efficiency," *FEBS Letters*, 473, 341-344.

* cited by examiner (VIIa) CBI conjugated to an MGB (VIIb) CPI conjugated to an MGB (VIIc) CPyI conjugated to an MGB (VIId) U-76,073

(VIIe) seco-adozelesin (VIIf) bizelesin (VIIg) CBI-TMI (VIIh) duocarmycin C2 (X=Cl)
(VIIi) duocarmycin B2 (X=Br)

(VIIj) seco-CC-1065

(VIIIa) etoposide (VIIIb) combretastatin A-4

(VIIIc) pancratistatin (VIIId) carminomycin (VIIIe) streptonigrin (VIIIf) zorubicin (VIIIg) elliptinium acetate (VIIIh) mitoxantrone (VIIIj) phenol mustard (VIIIi) daunorubicin (VIIIk) doxorubicin (VIIIl) SN-38

P-AMIDOBENZYLETHERS IN DRUG DELIVERY AGENTS

BACKGROUND OF THE INVENTION

1. Field of the Invention

The invention is in the field of pharmaceuticals, and provides drug conjugates as prodrugs for the delivery of drugs to cell populations, where the prodrugs are metabolized and activated by endogenous enzymes to provide active drugs.

2. Description of the Related Art

Metastatic carcinomas often express proteolytic enzymes including the cysteine protease cathepsin B (Demchik, L. L.; Sloane, B. F. Cell-Surface Proteases in Cancer. In *Proteases. New Perspectives;* A. Turk, Ed.; Birkhauser Verlag: Basel, 1999; pp 109–124; Mai, J.; Waisman, D. M.; Sloane, B. F. Cell Surface Complex of Cathepsin B/Annexin II Tetramer in Malignant Progression. *Biochim. Biophys. Acta* 2000, 1477, 215–230; Koblinski, J. E.; Ahram, M.; Sloane, B. F. Unraveling the Role of Proteases in Cancer. *Clin. Chim. Acta* 2000, 291, 113–135), matrix metalloproteinases such as collagenases and stromelysins (Davidson, A. H.; Drummond, A. H.; Galloway, W. A.; Whittaker, M. The Inhibition of Matrix Metalloproteinase Enzymes. *Chem. Industry* 1997, 258–261), and serine proteases, represented by plasminogen activator and plasmin (Andreasen, P. A.; Egelund, R.; Petersen, H. H. The Plasminogen Activation System in Tumor Growth, Invasion, and Metastasis. *Cell. Mol. Life Sci.* 2000, 57, 25–40). These enzymes are thought to be critically involved in the events that lead to metastasis, since they are capable of degrading the basement membranes and extracellular matrices around tumor tissues, allowing the tumor cells to migrate and invade into the surrounding stroma and endothelium. Additional activities associated with these proteases include participation in protease cascades, activation of enzymes and growth factors, and in tumor angiogenic stimulation.

Several investigators have explored the possibility of exploiting tumor-associated proteases for the development of new cancer chemotherapeutics. This has led to several promising orally active protease inhibitors having both preclinical and clinical antitumor activities (Davidson, A. H.; Drummond, A. H.; Galloway, W. A.; Whittaker, M. The Inhibition of Matrix Metalloproteinase Enzymes. *Chem. Industry* 1997, 258–261). An additional line of research involves the conscription of proteases for anticancer prodrug activation. Towards this end, peptide-containing anticancer prodrugs have been developed that are activated by proteases within solid tumors (Dubowchik, G. M.; Walker, M. A. Receptor-Mediated and Enzyme-Dependent Targeting of Cytotoxic anticancer Drugs. *Pharm. Ther.* 1999, 83, 67–123; Carl, P. L.; Chakravarty, P. K.; Katzenellenbogen, J. A.; Weber, M. J. Protease-Activated "Prodrugs" for Cancer Chemotherapy. *Proc. Natl. Acad Sci. USA* 1980, 77, 2224–2228; Chakravarty, P. K.; Carl, P. L.; Weber, M. J.; Katzenellenbogen, J. A. Plasmin-Activated Prodrugs for Cancer Chemotherapy. 1. Synthesis and Biological Activity of Peptidylacivicin and Peptidylphenylenediamine Mustard. *J. Med. Chem.* 1983, 26, 633–638; Chakravarty, P. K.; Carl, P. L.; Weber, M. J.; Katzenellenbogen, J. A. Plasmin-Activated Prodrugs for Cancer Chemotherapy. 2. Synthesis and Biological Activity of Peptidyl Derivatives of Doxorubicin. *J. Med. Chem.* 1983, 26, 638–644; Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341–3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg Med. Chem. Letts.* 1998, 8, 3347–3352; de Groot, F. M. H.; de Bart, A. C. W.; Verheijen, J. H.; Scheeren, H. W. Synthesis and Biological Evaluation of Novel Prodrugs of Anthracyclines for Selective Activation by the Tumor-Associated Protease Plasmin. *J. Med. Chem.* 1999, 42, 5277–5283; de Groot, F. M. H.; van Berkon, L. W. A.; de Bart, A. C. W.; Scheeren, H. W. Synthesis and Biological Evaluation of 2'-Carbonate-Linked and 2'-Carbonate-Linked Prodrugs of Paclitaxel: Selective Activation by the Tumor-Associated Protease Plasmin. *J. Med. Chem.* 2000, 43, 3093–3102; Greenwald, R. B.; Pendri, A.; Conover, C. D.; Zhao, H.; Choe, Y. H.; Martinez, A.; Shum, K.; Guan, S. Drug Delivery Systems Employing 1,4- or 1,6-Elimination: Poly(ethylene glycol) Prodrugs of Amine-Containing Compounds. *J. Med. Chem.* 1999, 42, 3657–3667; Putnam, D. A.; Shiah, J. G.; Kopecek, J. Intracellularly Biorecognizable Derivatives of 5-Fluorouracil. *Biochem. Pharm.* 1996, 52, 957–962; Harada, M.; Sakakibara, H.; Yano, T; Suzuki, T.; Okuno, S. Determinants for the Drug Release from T-0128, Camptothecin Analogue-Carboxymethyl Detran Conjugate. *J. Cont. Rel.* 2000, 69, 399–412; Denmeade, S. R.; Nagy, A.; Gao, J.; Lilja, H.; Schally, A. V.; Isaacs, J. T. Enzymatic Activation of a Doxorubicin-Peptide Prodrug by Prostate-Specific Antigen. *Cancer Res.* 1998, 58, 2537–2540; Loadman, P. M.; Bibby, M. C.; Double, J. A.; Al-Shakhaa, W. M.; Duncan, R. Pharmacokinetics of PK1 and Doxorubicin in Experimental Colon Tumor Models With Differing Responses to PK1. *Clin. Cancer Res.* 1999, 5, 3682–3688). Several of these agents have led to significant in vitro and in vivo antitumor activities.

There are two general approaches for attaching drugs to peptides for intratumoral proteolytic activation. In the first approach, the drug is appended directly to the peptide, leading to prodrugs that can either release the parent drug or release a drug that contains vestiges of the bound peptide (Putnam, D. A.; Shiah, J. G.; Kopecek, J. Intracellularly Biorecognizable Derivatives of 5-Fluorouracil. *Biochem. Pharm.* 1996, 52, 957–962; Harada, M.; Sakakibara, H.; Yano, T; Suzuki, T.; Okuno, S. Determinants for the Drug Release from T-0128, Camptothecin Analogue-Carboxymethyl Detran Conjugate. *J. Cont. Rel.* 2000, 69, 399–412; Denmeade, S. R.; Nagy, A.; Gao, J.; Lilja, H.; Schally, A. V.; Isaacs, J. T. Enzymatic Activation of a Doxorubicin-Peptide Prodrug by Prostate-Specific Antigen. *Cancer Res.* 1998, 58, 2537–2540). In the latter case, the released drug may have impaired cytotoxic activity. An additional consideration for direct drug attachment to peptides is the negative influence the drug can have on the kinetics of peptide hydrolysis.

To circumvent these potential shortcomings, a second approach has been developed that relies on the use of self-immolative spacers to separate the drug from the site of enzymatic cleavage. The incorporated spacer allows for the release of fully active, chemically unmodified drug from the conjugate upon amide bond hydrolysis. A commonly used spacer utilizes the bifunctional p-aminobenzyl alcohol group, which is linked to the peptide through the amine moiety, thereby forming an amide bond. Amine-containing drugs are attached through carbamate functionalities to the benzylic hydroxyl group of the p-amionobenzyl alcohol-based spacer. The resulting prodrugs are activated upon protease-mediated cleavage, leading to a 1,6-elimination reaction (Wakselman, M. 1,4- and 1,6-Eliminations from Hydroxy- and Amino-Substituted Benzyl Systems: Chemical and Biochemical Applications. *Nouveau J. Chim.* 1983, 7, 439–447) that splits off unmodified drug and carbon dioxide.

This methodology, based on the work of Sartorelli, Katzenellenbogen and coworkers (Teicher, B. A.; Sartorelli, A. C. Nitrobenzyl Halides and Carbamates as Prototype Bioreductive Alkylating Agents. *J. Med. Chem.* 1980, 23, 955–960; Carl, P. L.; Chakravarty, P. K.; Katzenellenbogen, J. A. A Novel Connector Linkage Applicable in Prodrug Design. *J. Med. Chem.* 1981, 24, 479–480) has been applied to plasmin catalyzed release of phenylenediamine mustard (Chakravarty, P. K.; Carl, P. L.; Weber, M. J.; Katzenellenbogen, J. A. Plasmin-Activated Prodrugs for Cancer Chemotherapy. 1. Synthesis and Biological Activity of Peptidylacivicin and Peptidylphenylenediamine Mustard. *J. Med. Chem.* 1983, 26, 633–638) and anthracyclines (Chakravarty, P. K.; Carl, P. L.: Weber, M. J.; Katzenellenbogen, J. A. Plasmin-Activated Prodrugs for Cancer Chemotherapy. 2. Synthesis and Biological Activity of Peptidyl Derivatives of Doxorubicin. *J. Med. Chem.* 1983, 26, 638–644; de Groot, F. M. H.; de Bart, A. C. W.; Verheijen, J. H.; Scheeren, H. W. Synthesis and Biological Evaluation of Novel Prodrugs of Anthracyclines for Selective Activation by the Tumor-Associated Protease Plasmin. *J. Med. Chem.* 1999, 42, 5277–5283; de Groot, F. M. H.; van Berkon, L. W. A.; de Bart, A. C. W.; Scheeren, H. W. Synthesis and Biological Evaluation of 2'-Carbonate-Linked and 2'-Carbonate-Linked Prodrugs of Paclitaxel: Selective Activation by the Tumor-Associated Protease Plasmin. *J. Med. Chem.* 2000, 43, 3093–3102) from their corresponding peptide-p-amidobenzyl carbamate derivatives, and also to release doxorubicin and mitomycin C from peptide-p-amidobenzyl carbamate peptide derivatives by lysosomal enzymes and cathepsin B (Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341–3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347–3352; Greenwald, R. B.; Pendri, A.; Conover, C. D.; Zhao, H.; Choe, Y. H.; Martinez, A.; Shum, K.; Guan, S. Drug Delivery Systems Employing 1,4- or 1,6-Elimination: Poly(ethylene glycol) Prodrugs of Amine-Containing Compounds. *J. Med. Chem.* 1999, 42, 3657–3667). The same linkage system has also been applied for the activation of anthracyclines in cells that were transfected with carboxypeptidase G2 (Niculescu-Duvaz, I.; Niculescu-Duvaz, D.; Fiedlos, F.; Spooner, R.; Martin, J.; Marais, R.; Springer, C. J. Self-Immolative Anthracycline Prodrugs for Suicide Gene Therapy. *J. Med. Chem.* 1999, 42, 2485–2489).

The chemistry used for drug attachment has generally been restricted to amine-containing drugs, with the exception of paclitaxel, which was linked through carbonates formed from hydroxyl groups at the 2' or 7-position (Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347–3352; de Groot, F. M. H.; van Berkon, L. W. A.; de Bart, A. C. W.; Scheeren, H. W. Synthesis and Biological Evaluation of 2'-Carbonate-Linked and 2'-Carbonate-Linked Prodrugs of Paclitaxel: Selective Activation by the Tumor-Associated Protease Plasmin. *J. Med. Chem.* 2000, 43, 3093–3102). Unlike many carbonates that are hydrolytically unstable, these paclitaxel 2' and 7-carbonates were quite stable in aqueous environments, consistent with what had already been reported for other paclitaxel carbonates (Ueda, Y; Matiskella, J. J.; Mikkilineni, A. B.; Farina, V.; Knipe, J. O.; Rose, W. C.; Casazza, A. M.; Vyas, D. M. Novel, Water-Soluble Phosphate Derivatives of 2'-Ethoxy Carbonylpaclitexel as Potential Prodrugs of Paclitaxel: Synthesis and Antitumor Evaluation *Bioorg. Med. Chem. Letts.* 1995, 5, 247–252; Senter, P. D.; Marquardt, H.; Thomas, B. A.; Hammock, B. D.; Frank, I. S.; Svensson, H. P. The Role of Rat Serum Carboxylesterase in the Activation of Paclitaxel and Camptothecin Prodrugs. *Cancer Res.* 1996, 56, 1471–1474). Many drugs containing reactive hydroxyl groups would not be expected to exhibit such high carbonate stability.

The present invention recognizes and addresses the need for broadly useful and versatile methodologies for attaching drugs, including anticancer drugs, to self-immolative spacers, which would lead to high serum stability and conditional drug release upon peptide bond hydrolysis.

SUMMARY OF THE INVENTION

In one aspect, the present invention provides compositions and methods which may be utilized to target a drug-ligand conjugate (prodrug) to a selected cell population, such as tumor sites, where the prodrug is enzymatically activated to release the drug. Based upon one aspect of the invention described herein, many drugs containing reactive hydroxyl groups may be converted into a prodrug form and in particular may be converted into a prodrug form capable of targeting a selected cell population, where these forms may have the desirable property of high stability in human serum. This new prodrug activation strategy is based on the remarkable and unexpected self-elimination reaction of aminobenzyl ethers as illustrated in Scheme 1.

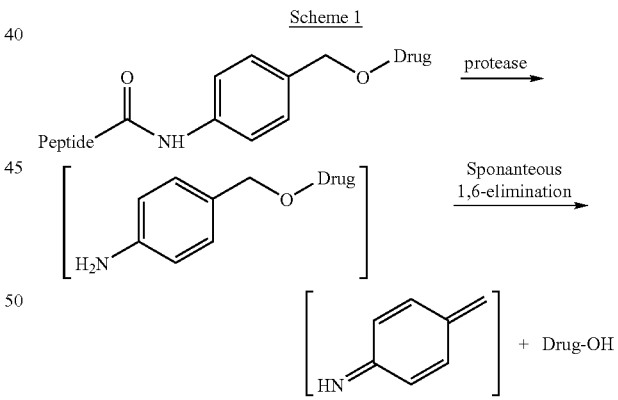

The drug conjugates of this invention comprise at least one drug moiety, and a prodrug linker. The prodrug linker is made up of an aminobenzyl ether-based self-immolative spacer, a peptide residue comprising a recognition/cleavage site for the enzymes, and optional moieties such as one or more of an acyl unit, and a second self-immolative spacer which separates the drug and the aminobenzyl ether spacer. In one aspect, the prodrug linker joins (links, couples) the drug residue to a ligand for a biological receptor. In another aspect, the prodrug linker has an N-terminus in addition to the terminus that is coupled to the drug residue, where the N-terminus is blocked by a protecting group. In one aspect, the drug conjugates may be represented by the general formulae (I) and (II)

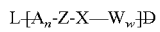  (I)

wherein: D is a drug residue; L is a ligand; A is an optional acyl unit; Z is a peptide residue comprising one or more amino acids; X is an aminobenzyl ether self-immolative group; W is an optional (second) self-immolative group; n is an integer of 0 or 1; and w is an integer of 0 or 1, where, $-[A_n-Z-X-W_w-]-$ represents a group referred to herein as a prodrug linker.

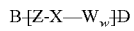  (II)

wherein: D is a drug residue; B is a blocking group; Z is a peptide residue comprising one or more amino acids; X is an aminobenzyl ether self-immolative group; W is an optional second self-immolative group; and w is an integer of 0 or 1, where $-[Z-X-W_w-]-$ represents a group referred to herein as the prodrug linker.

In a preferred aspect, the present invention provides a compound of the formula

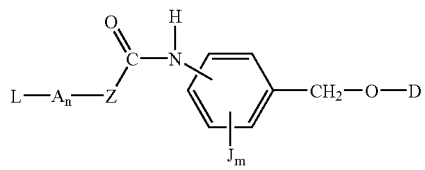

wherein: —O-D is a portion of a drug, where the drug has the formula HO-D, where in a preferred embodiment the HO— is joined to an aromatic ring of the drug residue D; J is an optional substituent, which is selected independently at each occurrence, and may occur as many as four times on the aromatic ring shown in the formula, and m is 0, 1, 2; 3 or 4;

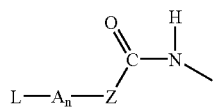

is situated at an ortho- or para-position with respect to the —$CH_2$— group; Z is a peptide residue comprising one or more amino acids; A is an acyl unit where n is 0 or 1; and L is a ligand.

In another preferred aspect, the present invention provides a compound of the formula

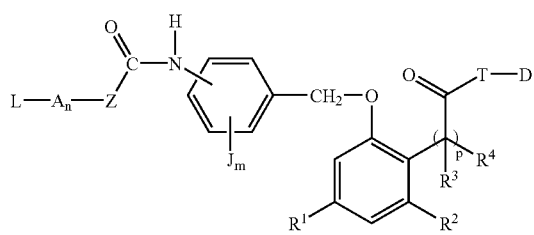

wherein: -T-D is a portion of a drug, where the drug has the formula HT-D; T is O, S, NH, or N(lower alkyl, i.e., $C_{1-6}$alkyl); J is a substituent group, and m is 0, 1, 2; 3 or 4;

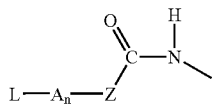

is situated at an ortho- or para-position with respect to the —$CH_2$— group; Z is a peptide residue comprising one or more amino acids; A is an acyl unit and n is 0 or 1; L is a ligand; p is 1 or 2; and each of $R^1$, $R^2$, $R^3$ and $R^4$ is independently selected from H and $C_1$–$C_5$ alkyl.

In another preferred aspect, the present invention provides a compound of the formula

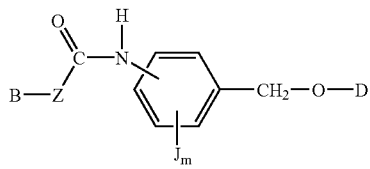

wherein: —O-D is a portion of a drug, where the drug has the formula HO-D, and in a preferred embodiment the HO— is joined to an aromatic ring of D; J is a substituent group, and m is 0, 1, 2; 3 or 4;

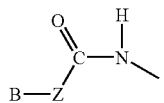

is situated at an ortho- or para-position with respect to the —$CH_2$— group; Z is peptide residue comprising one or more amino acids; and B is hydrogen or a blocking group selected from a D-amino acid and an N-terminus protecting group.

In another preferred aspect, the invention provides a compound of the formula

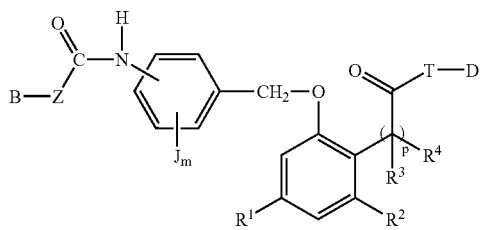

wherein: -T-D is a portion of a drug, where the drug has the formula HT-D; T is O, S, NH, or N(lower alkyl); J is a substituent group, and m is 0, 1, 2; 3 or 4;

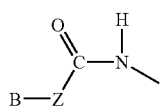

is situated at an ortho- or para-position with respect to the —CH$_2$— group; Z is an amino acid or a peptide; p is 1 or 2; and B is hydrogen or a blocking group selected from a D-amino acid and an N-terminus protecting group.

The above and other aspects of the present invention are achieved through derivatizing a drug by attaching it to a prodrug linker via a reactive functional group of the drug. In one aspect, the drug may be derivatized through a reactive functional group that is important for the biological activity of the drug thereby inhibiting or reducing the pharmacological activity of the drug to thereby convert the drug into a pharmacologically inactive or relatively inactive peptidyl derivative conjugate. The prodrug linker contains a peptide residue specifically tailored so as to render a drug conjugate of the present invention a selective substrate susceptible to enzymatic cleavage by one or more proteases, e.g., preferably lysosomal proteases, such as cathepsin B, C or D. The enzymatic cleavage reaction will remove the prodrug linker from the drug moiety by triggering the self-elimination of the aminobenzyl ether spacer group, and affect the release of the drug in its pharmacologically active form.

In one aspect, the present invention provides drug conjugates having superior serum stability. For example, in contrast to drug conjugates wherein a hydroxyl group of a drug is linked to a spacer via a labile carbonate linkage that is susceptible to rapid hydrolysis in aqueous buffer or human serum, the drug conjugates of the present invention utilizing a benzyl ether linkage are relatively more stable under the same conditions, and selectively undergo ether fragmentation to release the drug upon treatment with protease, e.g., cathepsin B. Serum stability is a desirable property for drug conjugates where it is desired to administer inactive drug to the patient's serum, have that inactive drug concentrate at a target by way of the ligand, and then have that drug conjugate converted to an active form only in the vicinity of the target.

In one aspect, the present invention provides drug conjugates that are characterized by the capability of the drug conjugate to target a selected cell population, for example, a tumor site. In one aspect, the drug conjugate comprises a ligand that is linked to a drug moiety through a prodrug linker. The ligand serves to deliver the drug conjugate to the desired target site by binding to a receptor distinctively associated with the cell population at the target site. In another aspect, the peptide residue of a ligand-free drug conjugate is a highly selective substrate for tumor specific enzymes that are present at the tumor site in sufficient amounts to generate cytotoxic levels of free drug in the proximity of the tumor.

Ideally, the toxic activity of the drug is greatly reduced or absent when the drug is bonded directly to the prodrug linker where the prodrug linker is further coupled with either a ligand or a blocking group. Because the free drug is only released in the proximity of a targeted cell population, the conjugates of the present invention provide both specificity and therapeutic drug activity for the treatment of the selected cell population. They may be used in a pharmaceutical composition, such as one comprising a pharmaceutically effective amount of a compound of Formula I or II below, in admixture with a pharmaceutically acceptable carrier, diluent or excipient.

In another aspect, the invention provides methods for treatment of cancers and other tumors in animal subjects. For instance, the invention provides compounds and compositions for use in a method for treating tumors wherein the animal subject is treated, in a pharmaceutically acceptable manner, with a pharmaceutically effective amount of a compound or composition of the present invention.

DETAILED DESCRIPTION OF THE INVENTION

Figure 1:
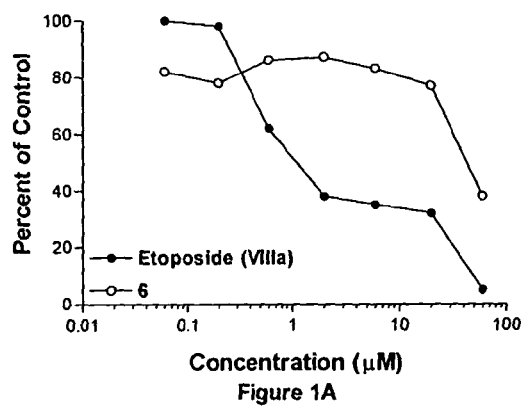
FIG. 1 is a graph showing the cytotoxic effects on L2987 human lung adenocarcinoma (A and D), WM266/4 (B), and IGR-39 (C) human melanoma cell lines. The cells were exposed to various concentrations of the drugs for 24 h, washed, incubated for a further 48 h, and the cytotoxic activities were quantified through the incorporation of [$^3$H] thymidine relative to untreated control cells.
Figure 1:
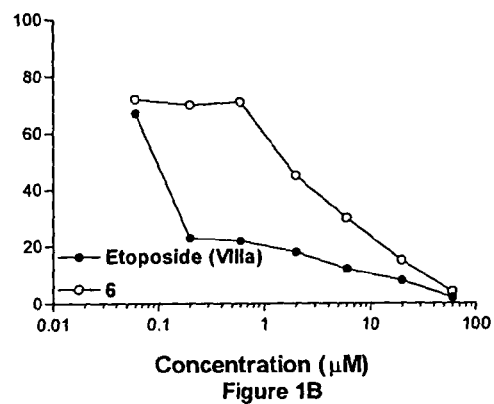
Figure 1:
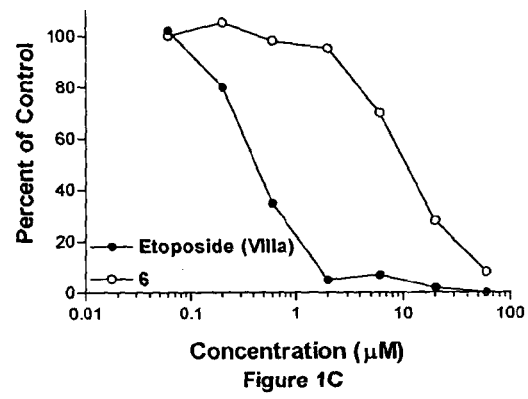
Figure 1:
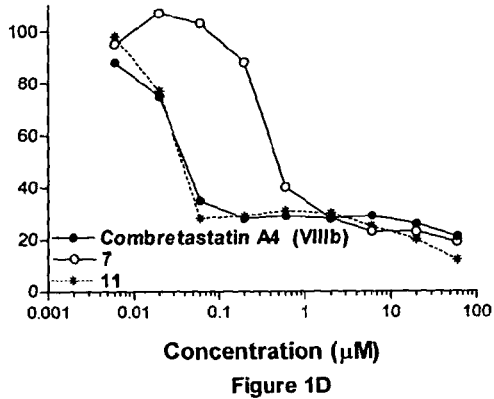
Figure 2A:
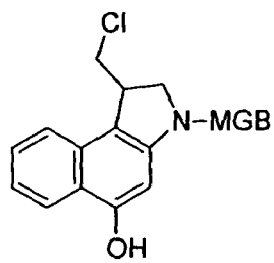
FIGS. 2A, 2B, 2C, 2D and 2E illustrate the chemical structures of exemplary drugs that may be incorporated into prodrugs of the present invention.
Figure 2A:
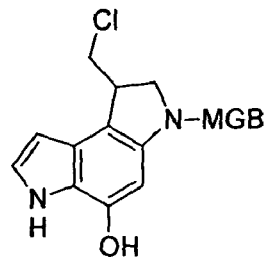
Figure 2A:
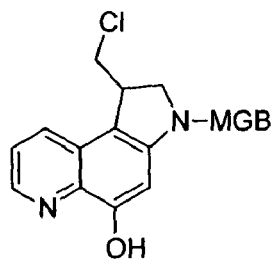
Figure 2A:
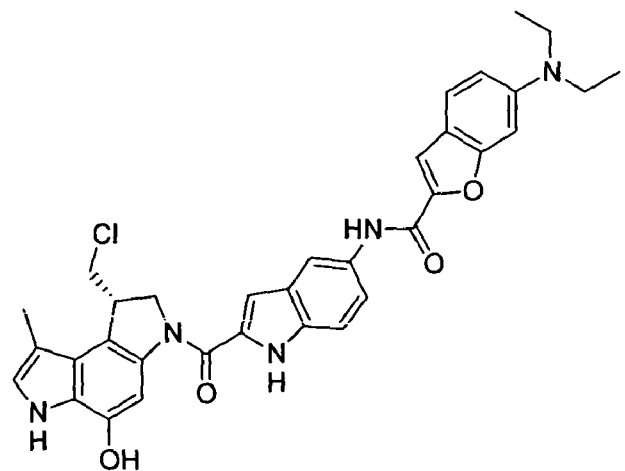
Figure 2B:
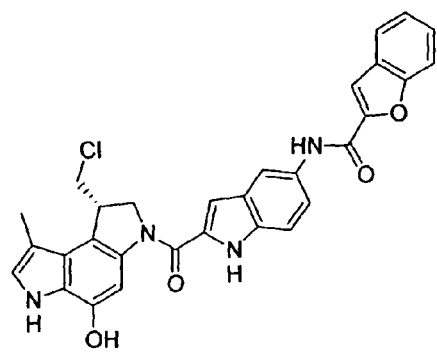
Figure 2B:
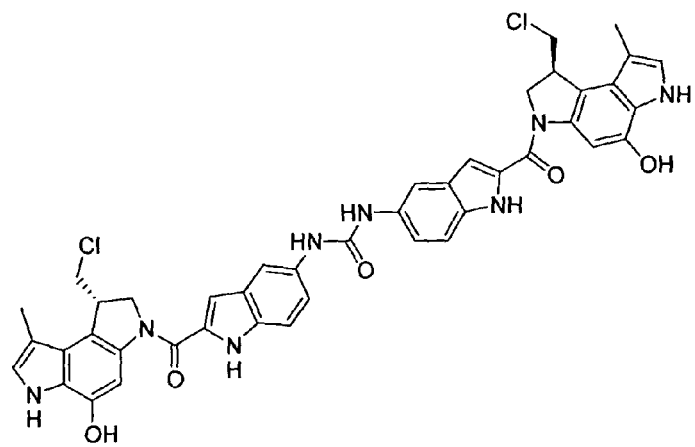
Figure 2B:
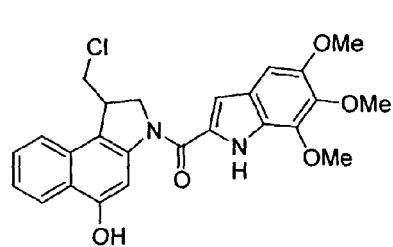
Figure 2B:
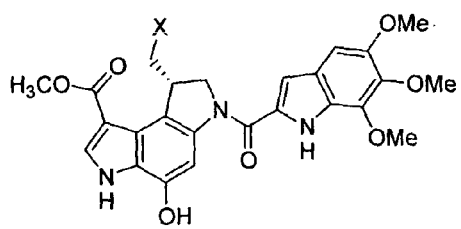
Figure 2C:
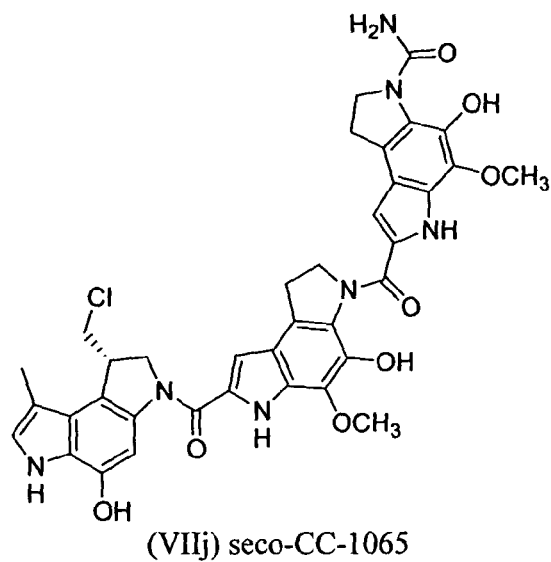
Figure 2C:
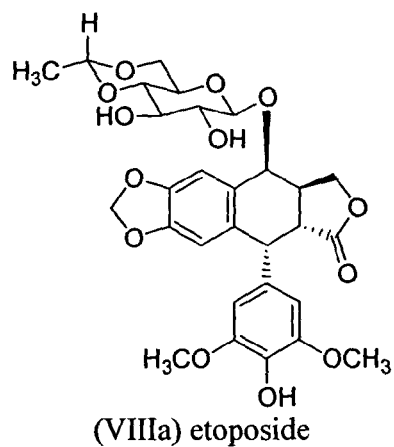
Figure 2C:
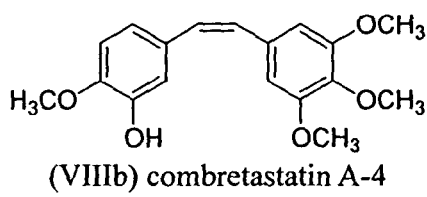
Figure 2C:
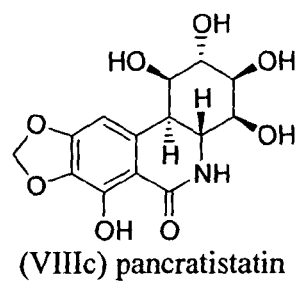
Figure 2D:
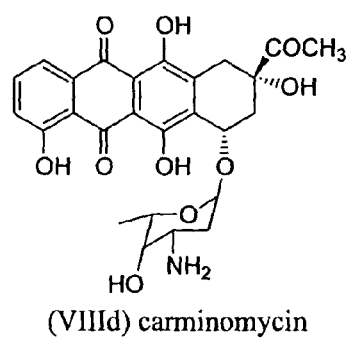
Figure 2D:
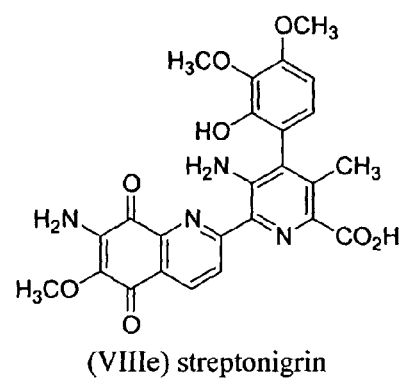
Figure 2D:
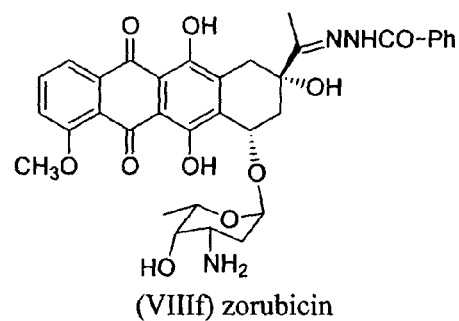
Figure 2D:
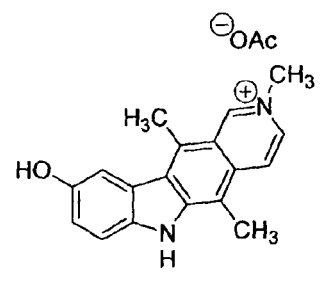
Figure 2E:
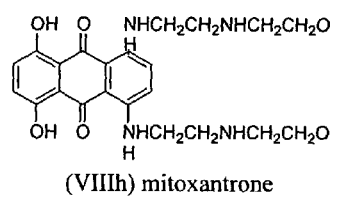
Figure 2E:
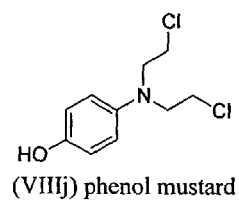
Figure 2E:
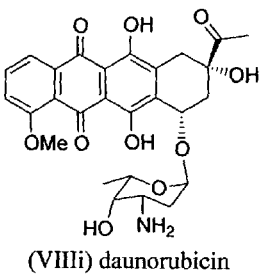
Figure 2E:
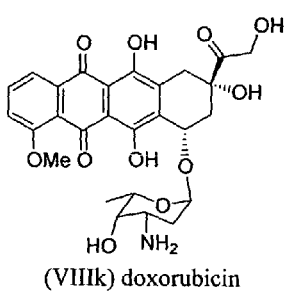
Figure 2E:
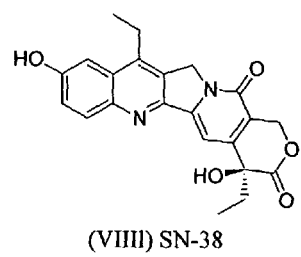

In one aspect, the present invention provides novel drug conjugates comprised of a ligand capable of targeting a selected cell population, and a drug connected to the ligand via a prodrug linker. The peptide-containing prodrug linker, shown as the group of chemical moieties within the square brackets in (I), is composed of an amino acid or a peptide residue (Z), an aminobenzyl ether self-immolative spacer (X), an optional acyl unit ($A_n$), and an optional second self-immolative spacer (W), which may separate the drug from the aminobenzyl ether group. Thus, the invention provides a conjugate represented by general formula (I):

wherein: D is a drug moiety; L is a ligand; A is an optional acyl unit; Z is an amino acid or a peptide residue; X is an aminobenzyl ether self-immolative group; W is an optional second self-immolative group; n is an integer of 0 or 1; and w is an integer of 0 or 1, where, –[$A_n$-Z—X—$W_w$]–represents a group referred to herein as a prodrug linker.

Another aspect of the invention provides drug conjugates wherein a blocking group is situated in the place of the ligand to protect the N-terminus of the peptide residue. Such drug conjugates may be selectively activated by enzymes naturally enriched in association with a selected cell population. Thus, the invention provides a conjugate represented by the general formula (II):

wherein: D is a drug moiety; B is a blocking group; Z is an amino acid or a peptide residue; X is an aminobenzyl ether self-immolative group; W is an optional second self-immolative group; and w is an integer of 0 or 1, where –[Z-X—$W_w$]–represents a group referred to herein as a prodrug linker.

In another aspect, the present invention provides a compound of the formula

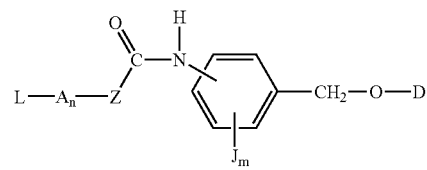

wherein: —O-D is a portion of a drug, where the drug has the formula HO-D and in a preferred embodiment the HO— is joined to an aromatic ring of D; J is a substituent group, and m is 0, 1, 2; 3 or 4;

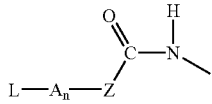

is situated at an ortho- or para-position with respect to the —CH$_2$— group; Z is an amino acid or a peptide; A is an acyl unit where n is 0 or 1; and L is a ligand.

In another aspect, the present invention provides a compound of the formula

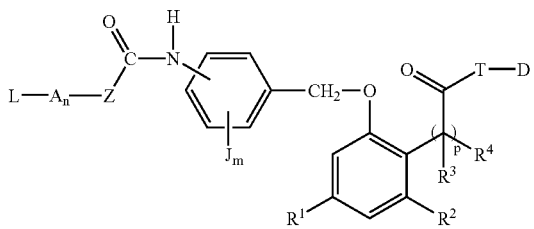

wherein: D is a drug comprising a T moiety; T is O, S, NH, or N(lower alkyl); J is a substituent group, and m is 0, 1, 2; 3 or 4;

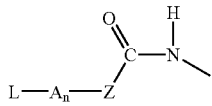

is situated at an ortho- or para-position with respect to the —CH$_2$— group; Z is an amino acid or a peptide; A is an acyl unit and n is 0 or 1; L is a ligand; p is 1 or 2; and each of R$^1$, R$^2$, R$^3$ and R$^4$ is independently selected from H and C$_1$–C$_5$ alkyl.

In another aspect, the present invention provides a compound of the formula

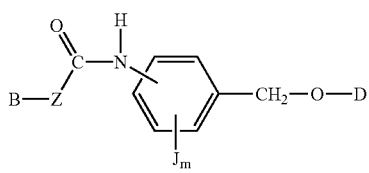

wherein: —O-D is a portion of a drug, where the drug has the formula HO-D and in a preferred embodiment the HO— is joined to an aromatic ring of D; J is a substituent group, and m is 0, 1, 2; 3 or 4;

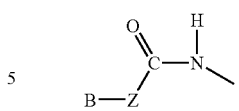

is situated at an ortho- or para-position with respect to the —CH$_2$— group; Z is an amino acid or a peptide; and B is hydrogen or a blocking group selected from a D-amino acid and an N-terminus protecting group.

In another aspect, the invention provides a compound of the formula

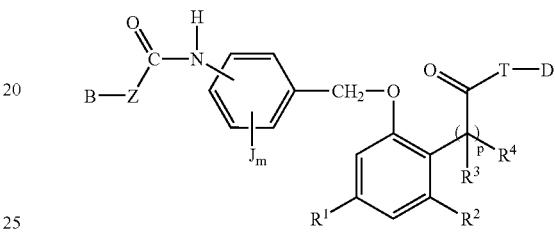

wherein: D is a drug comprising a T moiety; T is O, S, NH, or N(lower alkyl); J is a substituent group, and m is 0, 1, 2; 3 or 4;

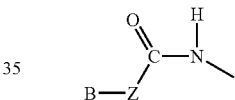

is situated at an ortho- or para-position with respect to the —CH$_2$— group; Z is an amino acid or a peptide; p is 1 or 2; and B is hydrogen or a blocking group selected from a D-amino acid and an N-terminus protecting group.

Before describing the present invention in further detail, the following terms as used herein are given the indicated meaning.

The term "prodrug" and the term "drug conjugate" are used herein interchangeably. Both refer to a compound that is relatively innocuous to cells while still in the conjugated form but which is selectively degraded to a pharmacologically active form by conditions, e.g., enzymes, located within or in the proximity of target cells.

The term "selective" as used in connection with enzymatic cleavage means a greater rate of cleavage of a peptidyl component of the instant invention relative to cleavage of a peptide residue which comprises a random sequence of amino acids. Therefore, the peptidyl component of the instant invention is a preferred substrate of the enzymes associated with the targeted cell population. The term "selective" also indicates that the peptide residue is cleaved at the site where it is coupled to the amino group of the aminobenzyl ether spacer.

The term "cytotoxic" means arresting the growth of, or killing, cells.

The term "hydroxylic drug" means a drug containing a hydroxyl group through which the drug may be coupled to the prodrug linker.

The term "aromatic" means a cyclic conjugated compound with all or some of the atoms in the ring being carbons.

The term "minor groove binder" is a molecule that binds to and/or within the minor groove of double stranded deoxyribonucleic acid (DNA).

The term "ligand" means any molecule that specifically binds or reactively associates or complexes with a receptor, substrate, antigenic determinant, or other binding site on a target cell or tissue. Examples of ligands include antibodies (e.g., a monoclonal antibody), enzymes (e.g., fibrinolytic enzymes), biologic response modifiers (e.g., interleukins, interferons, erythropeoitin, or colony stimulating factors), peptide hormones, and fragments thereof. The ligand can be linked directly, or through an acyl unit, to the peptide residue.

The term "blocking group" refers to an atom or a chemical moiety that protects the N-terminus of an amino acid or a peptide residue from undesired reactions via this reactive site. A blocking group used during the synthesis of a drug conjugate of the invention should remain attached to the N-terminus throughout the synthesis, and may be removed after completion of synthesis of the drug conjugate by chemical or other conditions that selectively achieve its removal. The blocking groups suitable for N-terminus protection are well known in the art of peptide chemistry. Exemplary blocking groups include, but are not limited to, hydrogen, D-amino acid, and carbobenzoxy (Cbz) chloride.

The term "peptide linker" in the present invention refers to the peptide moiety that links the drug moiety to the ligand in (I) or the blocking group in (II). The peptide linker is made up of an aminobenzyl ether self-immolative spacer, an amino acid or peptide residue, an optional acyl unit, and an optional second self-immolative spacer.

The term "self-immolative spacer" refers to a bifunctional chemical moiety which is capable of covalently linking together two spaced chemical moieties into a normally stable tripartate molecule. It will spontaneously separate from the second moiety if its bond to the first moiety is cleaved.

The terms "peptide residue" and "peptidic" refer to a single amino acid or a plurality of amino acids that are joined together by amide bonds.

The term "acyl" refers to an organic radical derived from a carboxylic acid by the removal of the hydroxyl group.

The term "acyl unit" means a bifunctional agent containing two distinctly reactive sites, one of which is a carboxylic acid or a reactive equivalent thereof. The carboxylic acid or reactive equivalent is joined to the N-terminus of the amino acid or a peptide residue through an amide linkage. The other reactive site of the acyl unit is coupled to the ligand of interest, such as an antibody. Examples of such "other" reactive sites include maleimides and haloacetamides that react with thiol groups on a ligand, e.g., mAbs; thiols that react with disulfides on a ligand, e.g., mAbs; active disulfides that react with thiols on a ligand; hydrazides that react with aldehydes and ketones on a ligand, e.g., mAbs, and hydroxysuccinimides, isocyanates, isothiocyanates, and anhydrides that react with amino groups on a ligand, e.g., mAbs.

In various aspects, the present invention provides: drug conjugates which are selectively activatable at the site of the tumor; tumor specific drug conjugates where the tumor specificity arises solely from the ligand; drug conjugates that are highly selective substrates for tumor specific enzymes, where these enzymes are present in the proximity of the tumor in sufficient amounts to generate cytotoxic levels of free drug in the vicinity of the tumor, and the ligand may optionally be omitted so that the N-terminus of the peptide residue is instead blocked using a conventional protecting group; tumor-specific drug conjugates that are stable to adventitious proteases in the human serum; tumor-specific drug conjugates in accordance with the preceding aspects, which are less toxic than the corresponding free drug; method for the production of drug conjugates and pharmaceutical compositions and methods for delivering the conjugates to target cells in which a modification in biological process is desired, such as in the treatment of diseases such as cancer; and a method for delivering to the site of tumor cells in a warm-blooded animal an active antitumor drug by administering to said warm-blooded animal the drug-ligand conjugate according to this invention.

In various preferred embodiments of the invention: the drug contains a reactive hydroxyl group, having a pKa of 16 or less; the drug contains a hydroxyl group joined to an aromatic moiety of the drug and this hydroxyl group is used to conjugate the drug to the remainder of the drug conjugate; the drug is 1,2,9,9a-tetra-hydro-cyclo-propa[c]benz[e]indol-4-one (CBI) conjugated to a minor groove binder (MGB); the peptide residue is valine-citrulline, the blocking group is carbobenzoxy (Cbz), and w is 0; the drug moiety is cyclopropapyrroloindole (CPI) conjugated to a minor groove binder, the peptide residue is valine-citrulline, the blocking group is carbobenzoxy (Cbz), and w is 0; the drug moiety is 1,2,9,9a-tetra-hydro-cyclo-propa[c]pyrido[3,2-e]indol-4-one (CPyI) conjugated to a minor groove binder (MGB), the peptide residue is valine-citrulline, the blocking group is carbobenzoxy (Cbz), and w is 0; the drug moiety is combretastatin A-4, the blocking group is carbobenzoxy (Cbz), the peptide residue is phenylalanine-lysine, the blocking group is carbobenzoxy (Cbz), and w is 0; the drug moiety is 1,2,9,9a-tetra-hydro-cyclo-propa[c]benz[e]indol-4-one (CBI) conjugated to a minor groove binder (MGB), the peptide residue is phenylalanine-lysine, the blocking group is carbobenzoxy (Cbz), and w is 0; the drug moiety is cyclopropapyrroloindole (CPI) conjugated to a minor groove binder, the peptide residue is phenylalanine-lysine, the blocking group is carbobenzoxy (Cbz), and w is 0; the drug moiety is 1,2,9,9a-tetra-hydro-cyclo-propa[c]pyrido[3,2-e]indol-4-one (CPyI) conjugated to a minor groove binder (MGB), the peptide residue is phenylalanine-lysine, the blocking group is carbobenzoxy (Cbz), and w is 0; the drug moiety is an anthracycline antibiotic, the ligand is an antibody, A is an acyl unit, the peptide residue is valine-citrulline, and w is 1; the drug moiety is taxol, the ligand is an antibody, A is an acyl unit, the peptide residue is valine-citrulline, and w is 1; the drug moiety is a mitomycin C, the ligand is an antibody, A is an acyl unit, the peptide residue is valine-citrulline, and w is 1; the drug moiety is an anthracycline antibiotic, the ligand is an antibody, A is an acyl unit, the peptide residue is phenylalanine-lysine, and w is 1; the drug moiety is taxol, the ligand is an antibody, A is an acyl unit, the peptide residue is phenylalanine-lysine, and w is 1; and the drug moiety is a mitomycin C, the ligand is an antibody, A is an acyl unit, the peptide residue is phenylalanine-lysine, and w is 1.

For a better understanding of the invention, the components of the inventive drug conjugates, i.e., the drugs, ligands, blocking groups, peptides and self-immolative groups, will be discussed individually below. The synthesis of the conjugates will then be described.

PRODRUG LINKER

The prodrug linker of the present invention covalently links the drug moiety to the ligand/blocking group in forming the drug conjugate of the present invention. The linker comprises a peptide residue, a self-immolative aminobenzyl ether spacer and an optional acyl unit. It may also contain a second self-immolative spacer W. Each of these components will now be described.

1. SELF-IMMOLATIVE SPACER

A drug conjugate in accordance with the present invention employs an aminobenzyl ether group,

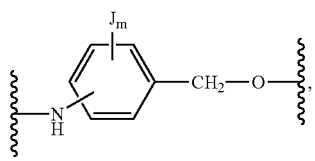

that functions as a self-immolative spacer. This group is denoted by the symbol "X" in the structures shown herein, e.g., in formulae I and II. In a preferred aspect, the aminobenzyl ether group covalently links a drug residue (via the ether group) to a peptide residue (via the amino group) to provide a tripartate molecule. This tripartate molecule is preferably stable and pharmacologically inactive in the absence of the target enzyme. However, upon action of the target enzyme, or any other suitable cleavage conditions, the bond indicated by the arrow in the figure below will be cleaved.

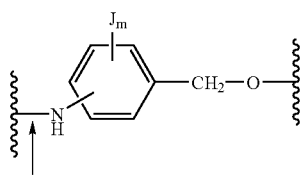

In one aspect, the amino group shown in the figure above is bonded to a carbonyl group. In another aspect, the amino group shown in the figure above in combination with the carbonyl group forms part of a peptidic linkage which is susceptible to enzyme-catalyzed cleavage. Upon such cleavage, whether by enzymatic or other means, e.g., hydrolysis means, the aminobenzyl ether group undergoes a spontaneous reaction that causes cleavage of the bond shown by the arrow in the figure

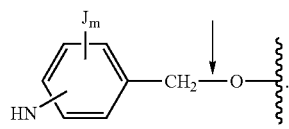

This cleavage leaves the oxygen of the ether group attached to the drug residue, thereby allowing reformation of the drug at the site of cleavage.

The line from the amine functionality of X into the ring of X indicates that the amine functionality may be bonded to any of the five carbons that both form the ring and are not substituted with the —CH$_2$—O— group that is necessarily bonded to the ring. Preferably, the amine functionality of X is covalently bound to the aromatic ring of the benzylether group at either the para, or at an ortho position on the ring, relative to the —CH$_2$O— group. Thus, in preferred aspects, X may be represented by formulae (III) and (IV).

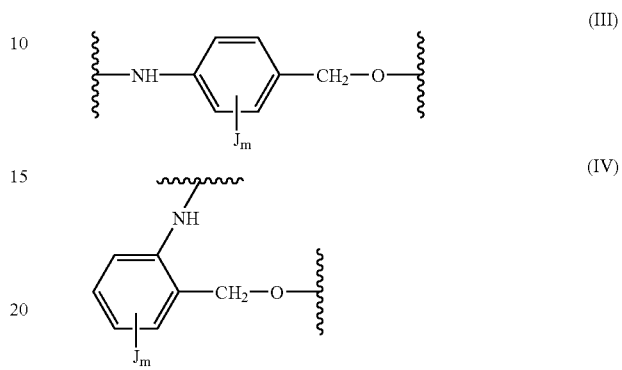

In one aspect, the X group is represented by formula (III), in another aspect the X group is represented by formula (IV), and in yet another aspect the X group is selected from formulae (III) and (IV).

The aromatic ring of the aminobenzyl ether group may optionally be substituted with one or more "J" groups. A "J" group is a substituent on the aromatic ring, which replaces a hydrogen that is otherwise attached to one of the four non-substituted carbons that form the ring. The J group, which may be a single atom, e.g., a halogen, or a multi-atom group, e.g., methyl, is selected in order to impact the stability of the aminobenzyl ether or the decomposition product thereof. Electron withdrawal from the ring may be used to facilitate the spontaneous decomposition of the aminobenzyl group from the drug after cleavage of the bond between the amino group of the aminobenzyl ether group and the adjacent peptide linkage. Exemplary J substituents include F, Cl, Br, NO$_2$, NHCOCH$_3$, N(CH$_3$)$_2$, NHCOCF$_3$, alkyl, and haloalkyl, where m is an integer of 0, 1, 2, 3 and 4.

A preferred self-immolative spacer suitable for use in the present invention is para-aminobenzyl ether wherein m is 0. Another preferred spacer suitable for use in the present invention incorporates an electron deficient group such as NO$_2$ at the meta position with respect to the benzyl ether. In one aspect, one nitro group is attached to the aromatic ring of the benzyl ether group.

When the drug has a hydroxyl group that may be used to link the drug to the remainder of the prodrug, then the aminobenzyl ether group may be linked directly to the drug residue. However, if the drug does not contain a hydroxyl group, but instead contains some other reactive functional group that may serve to link the drug to a self-immolative spacer, then such drugs may still be incorporated into an aminobenzyl ether-containing prodrug of the present invention by including a second, intermediate self-immolative spacer between the drug residue and the aminobenzyl ether group. The intermediate self-immolative spacer is denoted herein by the symbol "W".

In one aspect, the second spacer moiety W is represented by the formula (V)

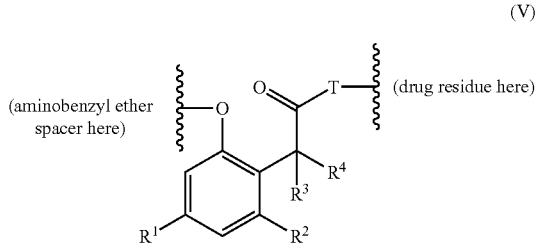

(V)

wherein, T is O, NH, N(lower alkyl) or S, p is 1 or 2, and each of $R^1$, $R^2$, $R^3$ and $R^4$ is independently selected from H and $C_1$–$C_5$ alkyl. The lower alkyl group has 1, 2, 3, 4, 5 or 6 carbons, i.e., is a $C_{1-6}$alkyl group. Such spacer groups are described in, for example, U.S. Pat. No. 6,210,345, where is incorporated herein by reference in its entirety for all purposes. The chemistry described in U.S. Pat. No. 6,210,345 to incorporate the group W into a drug conjugate may be employed to add an aminobenzyl ether to a drug conjugate according to the present invention.

2. PEPTIDE RESIDUE

In the conjugate of Formulae I and II, the peptide residue Z is the amidification residue of a single amino acid or a plurality of amino acids that are joined together by amide bonds. The peptide residue in a compound of the invention is selected with the goal of directing enzyme-catalyzed cleavage of an amide group that is joined to the amino group of the aminobenzyl ether spacer. The peptide residue may also be selected to be particularly responsive to an enzyme that is in a location of interest in a biological system. The peptide typically comprises 2–4 amino acid residues, however, more than 4 amino acid residues may be present in the peptide, e.g., 6 or 8. Peptide sequences that are susceptible to cleavage by specific enzymes or classes of enzymes are well known in the art.

The N-terminus of the peptide linker may be directly linked to a carboxyl functionality of a ligand, or may be indirectly bonded to a ligand via an acyl unit, as describe below.

The following group of exemplary peptide residue groups, are named in order to illustrate further the conjugates of the present invention: Phe-Lys, Val-Lys, Phe-Phe-Lys, D-Phe-Phe-Lys, Gly-Phe-Lys, Ala-Lys, Val-Cit, Phe-Cit, Leu-Cit, Ile-Cit, Trp-Cit, Phe-Ala, Gly-Phe-Leu-Gly [SEQ ID NO: 1], Ala-Leu-Ala-Leu [SEQ ID NO:2], Phe-$N^9$-tosyl-Arg, Phe-$N^9$-nitro-Arg. Some preferred peptide residues include one or any combination of Phe-Lys, Val-Lys, Val-Cit, and D-Phe-L-Phe-Lys.

Numerous specific peptide linker molecules suitable for use in the present invention can be designed and optimized for their selectivity for enzymatic cleavage by a particular tumor-associated protease. The preferred peptide linkers for use in the present invention are those that are optimized toward the proteases, such as cathepsin B. As described in further detail below, cathepsin B was shown to rapidly release the drug etoposide from a drug conjugate of the present invention at pH 5.1 at 37° C. (160 nmol/min/mg Cathepsin B), but in the absence of the added enzyme there was no breakdown of the conjugate after a week at pH 5.1 at 37° C.

3. ACYL UNIT

In the conjugates of Formula I, A is an optional acyl unit that joins Z to the ligand. The peptide group Z will typically terminate in an amino group. If the ligand has an amino-reactive group that may be used to incorporate the ligand into the prodrug, then the acyl unit is not necessary; although it may still be employed. However, if the ligand does not have an amino-reactive group, or does not contain an amino-reactive group that is desirably used to incorporate the ligand into the prodrug, then an acyl unit is conveniently included in a prodrug of the invention. The acyl unit contains an acyl group that may be reacted with the amino-terminus of the peptide linkage Z, and also contains a second reactive group that is reactive with a functional group on the ligand that is desirably used to incorporate the ligand into the prodrug. In other words, an acyl unit is defined as a bifunctional agent containing separate reactive sites, the first of which is a carboxylic acid or a reactive equivalent thereof. This first reactive site may be joined to the N terminus of an amino acid or a peptide residue through an amide linkage. The second reactive site is used to couple to the ligand of interest, such as antibodies.

Suitable bifunctional reactive linker groups are well known in the art, see S. S. Wong, Chemistry of Protein Conjugation and Cross-Linking, CRC Press, Inc., Boston, 1991. Exemplary second reactive sites are selected from maleimides and haloacetamides that may be used to react with thiol groups on a ligand, e.g., mAbs; thiols that react with disulfides on a ligand, e.g., mAbs; active disulfides that react with thiols on the ligand, e.g., mAb thiols; hydrazides that react with aldehydes and ketones on the ligand, e.g., mAbs, and hydroxysuccinimides, isocyanates, isothiocyanates, and anhydrides that react with amino groups on the ligand, e.g, mAbs.

A preferred acyl unit is the compound of formula (VI).

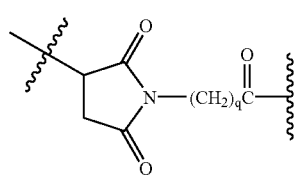

(VI)

wherein q is 1–10, or 3–6, or 5.

DRUG

As used herein, the terms "drug" or "D" refer to any compound possessing a desired biological activity and a reactive functional group that may be used to incorporate the drug into the conjugate of the invention. The desired biological activity includes the diagnosis, cure, mitigation, treatment, or prevention of disease in man or other animals. Thus, so long as it has the needed reactive functional group, the term "drug" refers to chemicals recognized as drugs in the official United States Pharmacopeia, official Homeopathic Pharmacopeia of the United States, or official National Formulary, or any supplement thereof. Exemplary drugs are set forth in the Physician's Desk Reference (PDR) and in the Orange Book maintained by the U.S. Food and Drug Administration (FDA). New drugs are being continually being discovered and developed, and the present invention provides that these new drugs may also be incorporated into a prodrug form of the present invention. Exemplary drugs are shown in FIGS. 2A–2E.

In various aspects of the invention the drug is: a cytotoxic drug useful in cancer therapy; a protein or polypeptide possessing a desired biological activity, such as a toxin, e.g., abrin, ricin A, pseudomonas exotoxin, and diphtheria toxin; other suitable proteins include tumor necrosis factor, α-interferon, β-interferon, nerve growth factor, platelet derived growth factor, and tissue plasminogen activator; and biological response modifiers such as, for example, lymphokines, interleukin-1 ("IL-1"), interleukin-2 ("IL-2"), interleukin6 ("IL-6"), granulocyte macrophage colony stimulating factor ("GM-CSF"), granulocyte colony stimulating factor ("G-CSF"), or other growth factors.

The drug conjugates as represented by formula I of the present invention are effective for the usual purposes for which the corresponding drugs are effective, and have superior efficacy because of the ability, inherent in the ligand, to transport the drug to the desired cells where it is of particular benefit.

The drug conjugates as represented by formula II of the present invention are effective for the usual purposes for which the corresponding drugs are effective, and have superior efficacy because they are capable of being selectively activated by enzymes associated with the cell population of interest.

In the drug conjugates of formulae I and II, when the only spacer is an aminobenzyl ether group (w=0), D is a drug that contains a hydroxyl group by means of which the drug is coupled to the aminobenzyl ether spacer group. Upon enzyme-activated fragmentation, as shown in Scheme 1, the aminobenzyl ether group decomposes to form an iminoquinone methide compound and the drug. It is speculated that initially upon decomposition, the drug is present in the form of an anion, i.e., a compound of the formula D-O$^-$, which is the conjugate base of a drug with the formula D-OH. Accordingly, as one factor in understanding the kinetics of the decomposition process, the stability of the D-O$^-$ structure may be considered important. Thus, in a preferred embodiment, the drug has a hydroxyl group that is relatively acidic, i.e., has a relatively stable conjugate base of the formula D-O$^-$. In various aspects of the invention, the pKa of the "linking" hydroxyl group of the drug is 16 or less, 15 or less, 14 or less, 13 or less, 12 or less, 11 or less, 10 or less, 9 or less, and typically, the pKa will be greater than 3, or greater 4, or greater than 5, where the invention includes each possible combination of the listed lower and upper pKa values.

In one aspect, the "linking" hydroxyl group, i.e., the hydroxyl group of the drug that is used to conjugate the drug to the aminobenzyl group, is attached to an aromatic ring. Typically, hydroxyl groups that are attached to aromatic rings have greater acidity than hydroxyl groups that are attached to an aliphatic group. Perhaps for this reason, drugs with aromatic ring-bound hydroxyl groups typically tend to decompose more rapidly than drugs with aliphatic bound hydroxyl groups in the conjugates of the present invention. Nevertheless, in one aspect of the invention, the hydroxyl group that links the drug to the conjugate is bonded to an aliphatic carbon of the drug.

Factors other than the acidity of a hydroxyl group may be important in describing the kinetics of the decomposition process. Another factor to be considered is the steric strain of the conjugate. In general, as the drug is more sterically confined by being conjugated in the prodrug form, the drug will more readily separate from the prodrug form upon decomposition of the aminobenzyl ether group.

Yet another factor to consider is the substitution on the aromatic ring of the aminobenzyl ether group, i.e., the choice of the J group. As that substitution is better able to stabilize the decomposition product and/or destabilize the drug conjugate, the substitution will be able to promote the decomposition process. Thus, with drugs that have relatively unstable D-O$^-$ forms, and/or that are not sterically strained in the prodrug form, it is preferred to select substitution for the aromatic ring of the aminobenzyl ether group such that the prodrug will more quickly decompose under the desired in vivo or in vitro conditions.

In one aspect, the drug used in the present invention is a cytotoxic drug, and particularly a cytotoxic drug that has demonstrated efficacy in cancer therapy. Representatives of such drugs are minor groove binders (MGBs), and MGB derivatives or analogs such as alkylated MGBs. Representative minor groove binders that may be formed into prodrugs according to the present invention include, without limitation, U-76,073, which has the chemical name (S)—N-[2[[1-(chloromethyl)-1,6-dihydro-5-hydroxy-8-methyl-benzo[1,2-b: 4,3-b']dipyrrol-3(2-yl]carbonyl]-1H-indol-5-yl]-6-(diethylamino)-2-benzofurancarboxamide; seco-adozelesin; bizelesin; 1,2,9,9a-tetra-hydro-cyclo-propa[c]-benz[e]indol-4-one-trimethoxyindole (CBI-TMI); duocarmycin C2; duocarmycin B2; and seco-CC-1065, which has the chemical name benzo(1,2-b:4,3-b')dipyrrole-3(2H)-carboxamide, 7-((1,6-dihydro-4-hydroxy-5-methoxy-7-((4,5,8,8a-tetrahydro-7-methyl-4-oxocyclopropa(c)pyrrolo(3,2-e)indol-2(1H)-yl)carbonyl)benzo(1,2-b:4,3-b')dipyrrol-3(2H)-yl)carbonyl)-1,6-dihydro-4-hydroxy-5-methoxy-, (7bR)-. Representative derivatives and analogs of MGBs include, without limitation, alkylated minor groove binders such as 1,2,9,9a-tetra-hydro-cyclo-propa[c]benz[e]indol-4-one (CBI) conjugated to an MGB; cyclopropapyrroloindole (CPI) conjugated to an MGB; and 1,2,9,9a-tetra-hydro-cyclo-propa[c]pyrido[3,2-e]indol-4-one (CPyI) conjugated to an MGB.

Another preferred group of cytotoxic agents for use as drugs in the present invention include, without limitation, etoposide; combretastatin A-4; pancratistatin; carminomycin; streptonigrin; zorubicin; elliptinium acetate; mitoxantrone; daunorubicin; phenol mustard; doxorubicin; and 7-ethyl-10-hydroxycamptothecin (SN-38). These drugs, along with the minor groove binders are represented by the formulae shown in FIG. 2A-2E.

Another preferred drug is auristatin E, (see U.S. Pat. No. 5,635,483), as shown below:

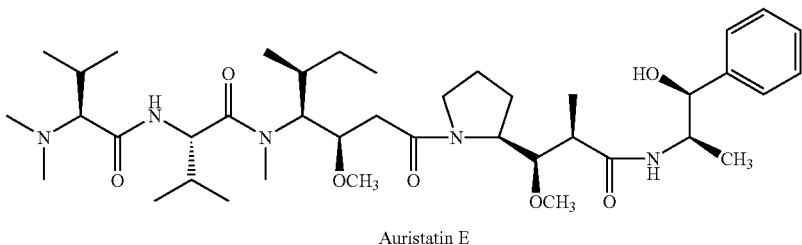
Auristatin E

In the drug conjugates of formula I and II, when a second self-immolative spacer (W) is present, D is a drug containing a chemically reactive functional group by means of which the drug is bonded to the peptide linker. The range of suitable reactive groups increases when "W" is present in a drug-conjugate of the invention. Said functional group may be selected from primary or secondary amine, hydroxyl, sulfhydryl, carboxyl, aldehyde and ketone.

Representative of said amino containing drugs are mitomycin-C, mitomycin-A, daunorubicin, doxorubicin, aminopterin, actinomycin, bleomycin, 9-amino camptothecin, $N^8$-acetyl spermidine, 1-(2 chloroethyl)-1,2-dimethane-sulfonyl hydrazide, tallysomycin, cytarabine and derivatives thereof. (See, U.S. Pat. No. 6,214,345). Other representative amino containing drugs are amino substituted CBI compounds, as shown by the following formulae:

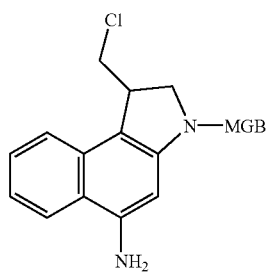
(IXa) 5-amino-CBI conjugated to an MGB

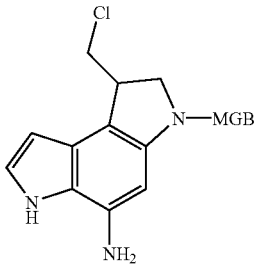
(IXb) 5-amino-CPI conjugated to an MGB

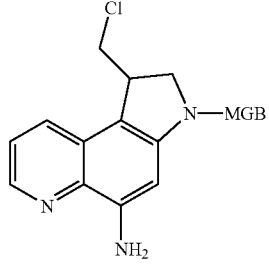
(IXc) 5-amino-CPyI conjugated to an MGB

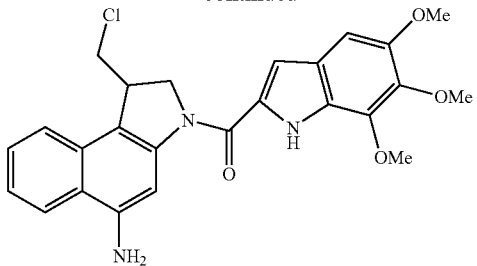
(IXb) 5-amino-CBI-TMI

Representative of said hydroxyl containing drugs are etoposide, camptothecin, taxol, esperamicin, 1,8-dihydroxy-bicyclo[7.3.1]trideca-4–9-diene-2,6-diyne-13-one, (U.S. Pat. No. 5,198,560), podophyllotoxin, anguidine, vincristine, vinblastine, morpholine-doxorubicin, N-(5,5-diacetoxy-pentyl) doxorubicin, auristatin E, and derivatives thereof.

Representative of said sulfhydryl containing drugs are esperamicin and 6-mercaptopurine, and derivatives thereof. Representative of said carboxyl containing drugs are methotrexate, camptothecin (ring-opened form of the lactone), butyric acid, retinoic acid, and derivatives thereof.

Representative of said aldehyde and ketone containing drugs are anguidine and anthracyclines such as doxorubicin, and derivatives thereof.

LIGAND

As used herein, a ligand is any molecule that specifically binds or reactively associates or complexes with a receptor or other receptive moiety associated with a given target cell population. It is preferred that the ligand, once in contact with its cellular binding site, promotes internalization of the conjugate. The internalizable ligand may be a peptide or protein growth factor, cytokine, tumor-specific antigen, hormone, transfer protein or antibody.

The immunoreactive ligands comprise an antigen-recognizing immunoglobulin (also referred to as an antibody), or an antigen-recognizing fragment thereof. Particularly preferred immunoglobulins are those that can recognize a tumor-associated antigen. As used herein, "immunoglobulin" may refer to any recognized class or subclass of immunoglobulins such as IgG, IgA, IgM, IgD, or IgE. Preferred are those immunoglobulins which fall within the IgG class of immunoglobulins. The immunoglobulin can be derived from any species. Preferably, however, the immunoglobulin is of human, murine, or rabbit origin.

Further, the immunoglobulin may be polyclonal or monoclonal, but is especially preferably monoclonal (mAb). Some preferred monoclonal antibodies include BR96 mAb (Trail, P. A., Willner, D., Lasch, S. J., Henderson, A. J., Hofstead, S. J., Casazza, A. M., Firestone, R. A., Hellström, I., Hellström, K. E., "Cure of Xenografted Human Carcinomas by BR96-Doxorubicin Immunoconjugates" *Science* 1993, 261, 212–215); mAbs against the Her2neu antigen such as Herceptin ("Herceptin (trastuzamab) in advanced breast cancer" *Cancer Treat Rev.* 26, 287–90, 2000); mAbs against the CD 40 antigen, such as S2C6 mAb (Francisco, J. A., Donaldson, K. L., Chace, D., Siegall, C. B., and Wahl, A. F. "Agonistic properties and in vivo antitumor activity of the anti-CD-40 antibody, SGN-14" *Cancer Res.* 2000, 60, 3225–3231); mAbs against the CD30 antigen, such as AC10 (Bowen, M. A., Olsen, K. J., Cheng, L., Avila, D., and Podack, E. R. "Functional effects of CD30 on a large granular lymphoma cell line YT" *J. Immunol.*, 151, 5896–5906, 1993); and mAbs against the CD27 antigen, such as CD70 (Lens, S. M., Drillenburg P. den Drijver, B. F., van Schijndel G, Pals S. T., van Lier R. A., van Oers M. H. "Aberrant expression and reverse signaling of CD70 on malignant B cells" *Br. J. Haematol.* 1996, 106(2), 491–503) Many other internalizing mAbs that bind to tumor associated antigens can be used in this invention, and have been reviewed (Franke, A. E., Sievers, E. L., and Scheinberg, D. A., "Cell surface receptor-targeted therapy of acute myeloid leukemia: a review" *Cancer Biother Radiopharm.* 2000,15, 459–76; Murray, J. L., "Monoclonal antibody treatment of solid tumors: a coming of age" *Semin Oncol.* 2000, 27, 64–70; Breitling, F., and Dubel, S., *Recombinant Antibodies*, John Wiley, and Sons, New York, 1998).

The non-immunoreactive protein, polypeptide, or peptide ligands which can be used to form the conjugates of this invention may include, but are not limited to, transferrin, epidermal growth factors ("EGF"), bombesin, gastrin, gastrin-releasing peptide, platelet-derived growth factor, IL-2, IL-6, tumor growth factors ("TGF"), such as TGF-α and TGF-β, vaccinia growth factor ("VGF"), insulin and insulin-like growth factors I and II. Non-peptidyl ligands may include, for example, carbohydrates, lectins, and apoprotein from low-density lipoprotein.

Alternatively, the ligand may be a soluble macromolecule that passively targets certain tumor cells through enhanced permeability and retention effect wherein the circulating macromolecules are selectively accumulated in tumor cells. These polymeric materials are effectively non-antigenic, i.e., they are nontoxic and will not elicit an appreciable immune response in mammals. The polymeric ligands included herein are preferably water-soluble at room temperature. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. As an alternative to polyalkylene oxide based polymers, effectively non-antigenic materials such as dextran, polyvinyl alcohols, (hydroxypropyl) methacrylamide, chitins, styrene-co-maleic acid/anhydride, and polyamino acids such as polyglutamic acid and polylysine can be used.

PREPARATION OF THE CONJUGATES

The peptide derivative, Cbz-valine-citrulline-p-aminobenzyl alcohol (1, Cbz-val-cit-PAB-OH) has previously been used for the preparation of Cbz-val-cit-PAB-doxorubicin carbamate, a compound that released active doxorubicin upon treatment with cathepsin B (Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341–3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347–3352). The drug was attached to the peptide through a carbamate linkage as shown in Scheme 2 (Y=NH).

Scheme 2

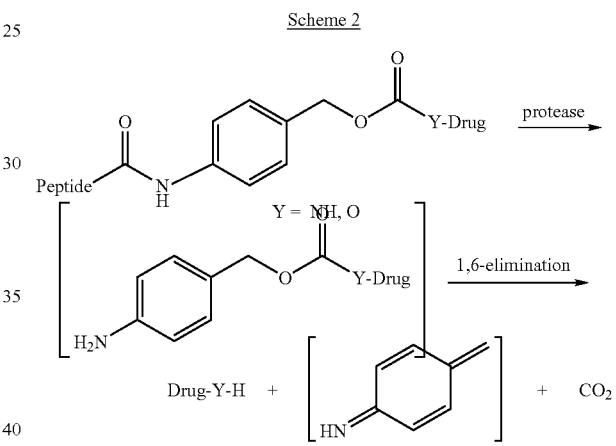

To explore the potential of using this drug elimination pathway for cleaving less labile bonds, ether derivatives of 1 were prepared using either the Mitsunobu reaction to form the naphthol ether 2, or the two-step imidate-substitution reaction to form the N-acetylnorephedrine derivative 5 (Scheme 3).

Scheme 3

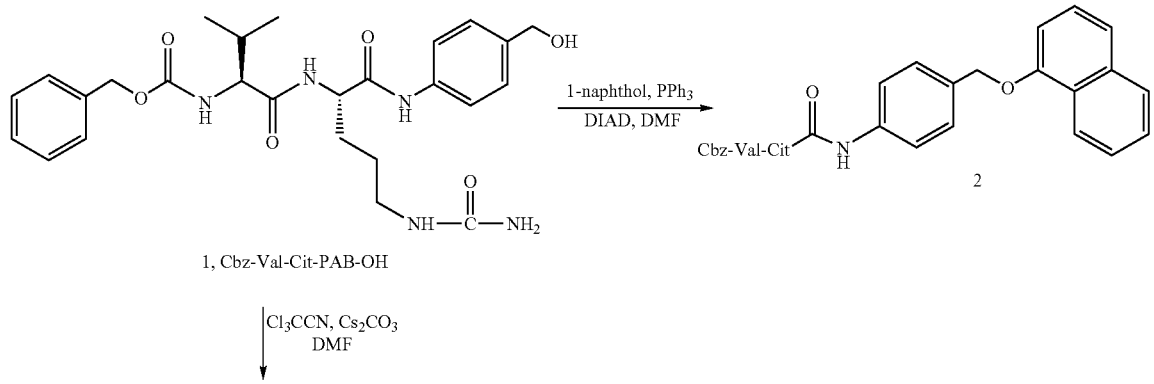

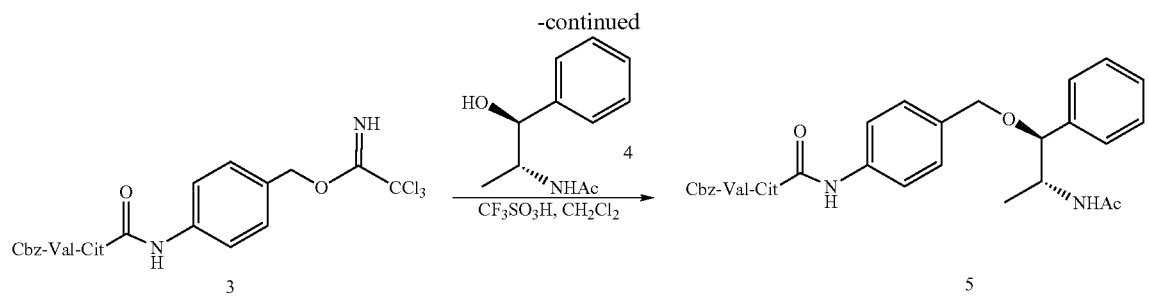

These compounds were designed to model anticancer drugs that contain chemically related moieties. HPLC analysis indicated that the naphthol ether 2 was a substrate for bovine spleen cathepsin B, and that the products formed were naphthol and Cbz-val-cit-COOH. The reaction proceeded rapidly (350 nmol/min/mg cathepsin B), but in the absence of added enzyme there was no breakdown of the starting material after 1 week at 37° C. at pH 5.1, 7.2, and in pooled human serum (Table I). The present invention provides the first indication that p-aminobenzyl ethers are capable of undergoing 1,6-elimination reactions.

Similar studies undertaken with the N-acetylnorephedrine ether 5 demonstrated that the compound was hydrolyzed by cathepsin B, leading to the release of Cbz-val-cit-COOH as expected. However, no N-acetylnorephedrine was detected, suggesting that the p-aminobenzyl ether formed after peptide bond cleavage did not undergo further fragmentation. Thus, the nature of the leaving group attached to the p-aminobenzyl group affects the 1,6-elimination reaction. It is speculated, however, that a more electron negative substituent at the α position of the hydroxyl group may facilitate the fragmentation. For example, if —NHAc is replaced by —F, the inductive effect of the strongly electron negative group F is capable of stabilizing the intermediate conjugate base resulted from the fragmentation.

On the basis of these results, the anticancer drugs etoposide (VIIIa) and combretastatin A-4 (VIIIb) were linked to 1 using the coupling conditions shown in Scheme 4.

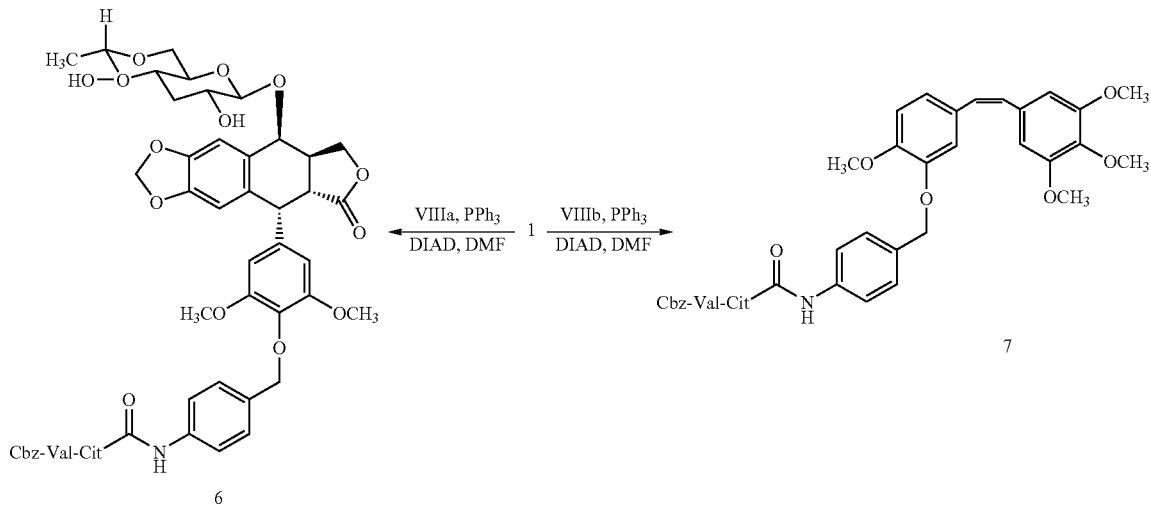

Scheme 4

Etoposide is a clinically approved topoisomerase inhibitor that has demonstrated utility in chemotherapeutic combinations for the treatment of leukemia, lymphoma, germ cell tumors, small cell lung tumors and several other carcinomas (Hande, K. R. Etoposide: Four Decades of Development of a Topoisomerase II Inhibitor. *Eur. J. Cancer* 1998, 34, 1514–1521). Combretastatin A-4 is a promising antiangiogenic agent that inhibits the polymerization of tubulin (Horsman, M. R.; Murata, R.; Breidahl T.; Nielson, F. U.; Maxwell, R. J.; Stodkiled-Horgensen, H.; Overgaard. Combretastatins Novel Vascular Targeting Drugs for Improving Anti-Cancer Therapy. Combretastatins and Conventional Therapy. *J. Adv. Exp. Med. Biol.* 2000, 476, 311–323). Treatment of 6 and 7 with cathepsin B led to the release of etoposide (VIIIa) and combretastatin A-4 (VIIIb), respectively (Table I). Both peptide derivatives were stable at pH 5.1, 7.2, and in human serum.

For comparison, the carbonate derivatives 10 and 11 were prepared from acetylnorephedrine (4) and combretastatin A-4 (VIIIb), respectively (Scheme 5).

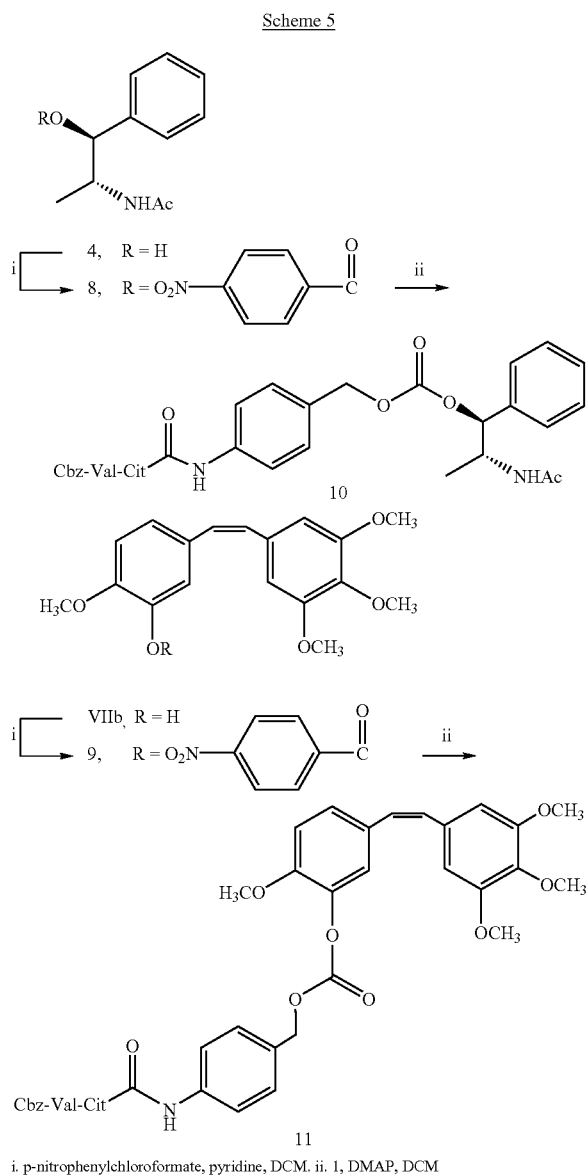

Scheme 5 i. p-nitrophenylchloroformate, pyridine, DCM. ii. 1, DMAP, DCM

Both carbonates 10 and 11 proved to be unstable in aqueous environments, in contrast to the corresponding ethers 5 and 7, respectively.

As expected enzymatic hydrolysis of 10 and 11 led to the formation of 4 and VIIIb. It is noteworthy that there were no significant kinetic differences in cathepsin B mediated hydrolyses of the peptide-carbonate and peptide-ether derivatives. Thus, peptide derivatives of p-aminobenzyl aromatic ethers are stable in neutral or slightly acidic buffers, and undergo facile ether fragmentation upon treatment with an enzyme that cleaves the amide bond.

In vitro cytotoxicity were performed on cancer cell lines to determine if the peptide derivatives acted as prodrugs. The cell lines (L2987 human lung adenocarcinoma, WM266/4 and IGR-39 human melanomas) were exposed to the agents for 24 h, washed, and viability was determined two days later by measuring the incorporation of $^3$H-thymidine compared to the untreated controls. There were significant differences in the cytotoxic activity etoposide (VIIIa) and the corresponding peptide ether derivative (6) on all three cell lines (FIG. 1A-C). Etoposide (VIIIa) was 15–22 times more active than 6, a result consistent with the loss in cytotoxic activity that has been reported with another phenol derivatives of etoposide (Senter, P. D.; Saulnier, M. G.; Schreiber, G. J.; Hirschberg, D. L.; Brown, J. P.; Hellströ, I.; Hellströ, K. E. Anti-Tumor Effects of Antibody-Alkaline Phosphatase Conjugates in combination with Etoposide Phosphate. *Proc. Natl. Acad. Sci. USA* 1988, 85, 4842–4846). Similarly, the combretastatin ether (7) was less potent than combretastatin A-4 (VIIIb) by a factor of 13 on L2987 human lung adenocarcinoma cells (FIG. 1D). Significantly, the combretastatin A-4 carbonate derivative 11 was as cytotoxic as combretastatin A-4 (VIIIb), reflecting the inherent instability of carbonate compared to the ether linkages (Table I). These results, taken together with the enzyme hydrolysis studies, indicate that the peptide ether drug derivatives are prodrugs that can be activated by cathepsin B.

COMPOSITIONS

In other aspects, the present invention provides prodrugs comprising a novel aminobenzyl ether spacer as described above, in combination with a pharmaceutically acceptable carrier, excipient, or diluent. Thus, the present invention provides a pharmaceutical or veterinary composition (hereinafter, simply referred to as a pharmaceutical composition) containing a prodrug of the invention as described above, in admixture with a pharmaceutically acceptable carrier. The invention further provides a composition, preferably a pharmaceutical composition, containing an effective amount of a prodrug as described above, in association with a pharmaceutically acceptable carrier.

The pharmaceutical compositions of the present invention may be in any form that allows for the composition to be administered to an animal subject. For example, the composition may be in the form of a solid, liquid or gas (aerosol). Typical routes of administration include, without limitation, oral, topical, parenteral, sublingual, rectal, vaginal, ocular, and intranasal. The term parenteral as used herein includes subcutaneous injections, intravenous, intramuscular, intrastermal injection or infusion techniques. Pharmaceutical compositions of the invention are formulated so as to allow the active ingredients contained therein to be bioavailable upon administration of the composition to an animal subject. Compositions that will be administered to a subject take the form of one or more dosage units, where for example, a tablet may be a single dosage unit, and a container of a compound of the invention in aerosol form may hold a plurality of dosage units.

Materials used in preparing the pharmaceutical compositions should be pharmaceutically pure and non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the particular form of the active ingredient, the manner of administration, and the composition employed.

In general, the pharmaceutical composition includes an (where "a" and "an" refers here, and throughout this specification, as one or more) active compounds of the invention in admixture with one or more carriers. The carrier(s) may be particulate, so that the compositions are, for example, in tablet or powder form. The carrier(s) may be liquid, with the compositions being, for example, an oral syrup or injectable liquid. In addition, the carrier(s) may be gaseous, so as to provide an aerosol composition useful in, e.g., inhalatory administration.

When intended for oral administration, the composition is preferably in either solid or liquid form, where semi-solid, semi-liquid, suspension and gel forms are included within the forms considered herein as either solid or liquid.

As a solid composition for oral administration, the composition may be formulated into a powder, granule, compressed tablet, pill, capsule, chewing gum, wafer or the like form. Such a solid composition will typically contain one or more inert diluents or edible carriers. In addition, one or more of the following adjuvants may be present: binders such as carboxymethylcellulose, ethyl cellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the composition is in the form of a capsule, e.g., a gelatin capsule, it may contain, in addition to materials of the above type, a liquid carrier such as polyethylene glycol, cyclodextrin, or a fatty oil.

The composition may be in the form of a liquid, e.g., an elixir, syrup, solution, emulsion, or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition for administration by injection, one or more of a surfactant, preservative, wetting agent, dispersing agent, suspending agent, buffer, stabilizer, and isotonic agent may be included.

The liquid pharmaceutical compositions of the invention, whether they are solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of the present invention such that a suitable dosage will be obtained. Typically, this amount is at least 0.01% of a compound of the invention in the composition however the precise dose will depend in large part on the drug selected for incorporation into the inventive conjugates. When intended for oral administration, this amount may be varied to be between 0.1% and about 80% of the weight of the composition. Preferred oral compositions contain between about 4% and about 50% of the compound of the invention. Preferred compositions and preparations according to the present invention are prepared so that a parenteral dosage unit contains between 0.01% to 2% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of a compound of the present invention of from about 0.1% to about 10% w/v (weight per unit volume).

The composition may be intended for rectal administration, in the form, e.g., of a suppository which will melt in the rectum and release the drug. The composition for rectal administration may contain an oleaginous base as a suitable nonirritating excipient. Such bases include, without limitation, lanolin, cocoa butter and polyethylene glycol.

The composition may include various materials that modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the present invention may consist of gaseous dosage units, e.g., it may be in the form of an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, spacers and the like, which together may form a kit. Preferred aerosols may be determined by one skilled in the art, without undue experimentation.

Whether in solid, liquid or gaseous form, the pharmaceutical composition of the present invention may contain one or more known pharmacological agents used in the treatment of cancer.

The pharmaceutical compositions may be prepared by methodology well known in the pharmaceutical art. For example, a composition intended to be administered by injection can be prepared by combining a compound of the invention with water so as to form a solution. A surfactant may be added to facilitate the formation of a homogeneous solution or suspension. Surfactants are compounds that non-covalently interact with a compound of the invention so as to facilitate dissolution or homogeneous suspension of the active compound in the aqueous delivery system.

BIOLOGICAL ACTIVITY AND UTILITY OF COMPOUNDS

The present invention provides biologically-active compounds, and methods of preparing the compounds of the invention, pharmaceutical compositions comprising the compounds of the invention, and methods for treatment of cancers and other tumors in animal subjects. For instance, the invention provides compounds and compositions for use in a method for treating tumors wherein the animal subject is treated, in a pharmaceutically acceptable manner, with a pharmaceutically effective amount of a compound or composition of the present invention.

The compounds and compositions of the invention can be used in a variety of settings for the treatment of mammalian cancers. The antibody conjugates can be used to deliver the cytotoxic drug to tumor cells. Once the antibody has bound to tumor-associated antigens, it is taken up inside cells through receptor-mediated endocytosis into endosomes and lysosomes. The endogenous enzymes such as proteases selectively cleave the linkage between the peptide and the aminobenzyl ether spacer, triggering the spacer group to self eliminate. The released drug is then free to migrate in the cytosol and induce cytotoxic activities.

The specificity of the mAb for a particular tumor type will dictate which tumors will be treated with the immunoconjugates. For example, BR96 containing conjugates will be used to treat antigen positive carcinomas including those of the lung, breast, colon, ovaries, and pancreas. Anti-CD30- and anti-CD40-containing conjugates may be used for treating hematologic malignancies.

Conjugation of these highly potent drugs to monoclonal antibodies specific for tumor markers results in specific targeting, thus reducing general toxicity of these compounds. Likewise, the ligand free drugs are designed to be highly selective substrates to tumor associated enzymes that are naturally enriched at the tumor sites, thus allowing the fully active drug to be released only at the vicinity of the tumor cells.

EXAMPLES

General Methods. Commercially available reagents and solvents were obtained as follows: HPLC-grade solvents, Fisher; anhydrous solvents, Aldrich; diisopropyl azodicarboxylate (DIAD, 95%), Lancaster; 4-aminobenzyl alcohol, Alfa Aesar; Z-val-OSu, Advanced ChemTech; L-citrulline, Novabiochem; (1S, 2R)-(+)-norephedrine and other commercially available reagents, Aldrich. Cbz-val-cit-PAB-OH (1) (Dubowchik, G. M.; Firestone, R. A. Cathepsin B-Sensitive Dipeptide Prodrugs. 1. A Model Study of Structural Requirements for Efficient Release of Doxorubicin. *Bioorg. Med. Chem. Letts.* 1998, 8, 3341–3346; Dubowchik, G. M.; Mosure, K.; Knipe, J. O.; Firestone, R. A. Cathepsin B-Sensitive Dipeptide Prodrugs. 2. Models of Anticancer Drugs Paclitaxel (Taxol), Mitomycin C and Doxorubicin. *Bioorg. Med. Chem. Letts.* 1998, 8, 3347–3352) and combretastatin A-4 (VIIIb) (Pettit, G. R.; Singh, S. B.; Boyd, M. R.; Hamel, E.; Pettit, R. K.; Schmidt, J. M.; Hogan, F. Antineoplastic Agents. 291. Isolation and Synthesis of Combretastatin A-4, A-5, and A-6. *J Med. Chem.* 1995, 38, 1666–1672) were synthesized as previously described. $^1$H NMR spectra were recorded on a Varian Gemini 300 MHz spectrophotometer. Flash column chromatography was performed using 230–400 mesh ASTM silica gel from EM Science. Analtech silica gel GHLF plates were used for thin-layer chromatography. HPLC was performed using a Waters Alliance system with a photodiode array detector. Combustion analyses were determined by Quantitative Technologies, Inc., Whitehouse, N.J.

General Procedure for the Mitsunobu Reaction. Peptide 1 (1.0 eq), triphenylphosphine (1.1 eq) and the appropriate phenol (1.0–1.1 eq) were dissolved in DMF/toluene (1:1) and evaporated to dryness under high vacuum. The residue was taken up in dry DMF while under $N_2$ and cooled to 0° C. DIAD (1.1 eq) was added dropwise over 1 min while stirring. The yellow/brown solution was monitored by TLC (9:1 $CH_2Cl_2$-MeOH). An additional 1.1 eq of $PPh_3$ and DIAD was added after 4 h. The solution was stirred for a total of 16–24 h, followed by solvent removal in vacuo. The resulting product was purified by chromatography on silica gel (eluent gradient: 100% $CH_2Cl_2$ to 9:1 $CH_2Cl_2$-MeOH). The desired fractions were pooled and concentrated to a white or off-white solid. Further purification could be obtained by triturating with ether.

Example 1

CBZ-VAL-CIT-PAB-1-O-NAPHTHOL (2)

$R_f$ 0.26 (9:1 $CH_2Cl_2$-MeOH); mp 175 (dec); UV $\lambda_{max}$ 215, 242, 305 nm; LRMS (ESI$^+$) m/z 640.3 (M+H)$^+$, 662.2 (M+Na)$^+$, 678.2 (M+K)$^+$; $^1$H NMR (DMSO-d$_6$) δ8.19–8.24 (2 H, m, aromatic), 7.80–7.87 (2 H, m, aromatic), 7.06–7.50 (13 H, m, aromatic), 6.76 (1 H, d, J=7.8 Hz, aromatic), 5.07 (2 H, s, Cbz-CH$_2$), 4.44–4.50 (1 H, m, val-CH), 4.28 (2 H, s, PAB-CH$_2$), 3.95 (1 H, d, J=6.9 Hz, cit-CH), 3.03–3.20 (2 H, m, cit-NCH$_2$), 1.95–2.10 (1 H, m, val-CH), 1.28–1.178 (4 H, m, cit-CH$_2$'s), 0.96 (3 H, d, J=6.9 Hz, val-CH$_3$), 0.93 (3 H, d, J=6.9 Hz, val-CH$_3$). Anal. ($C_{36}H_{41}N_5O_6 \cdot H_2O$) C, H, N.

Example 2

CBZ-VAL-CIT-PAB-O-TRICHLOROACETAMIDATE (3)

Peptide 1 (100 mg, 0.19 mmol) was dissolved in anhydrous DMF to which cesium carbonate (13 mg, 4 μmol, 0.2 eq) was added. While under $N_2$, trichloroacetonitrile (0.2 mL, 1.9 mmol, 10 eq) was added, and the contents stirred while monitoring by TLC (9:1 $CH_2Cl_2$-MeOH). Reaction was complete after 16 h. The mixture was filtered and filtrate concentrated and subject to chromatography on $SiO_2$ (eluent gradient 100% $CH_2Cl_2$ to 9:1 $CH_2Cl_2$-MeOH containing 1% triethylamine). The desired fractions were pooled and evaporated to an off-white powder (99 mg, 77%): $R_f$ 0.44 (9:1 $CH_2Cl_2$-MeOH); UV $\lambda_{max}$ 215, 250 nm; LRMS (ESI$^+$) m/z 679.3 (M+Na)$^+$, 681.2 (M+2+Na)$^+$, 683.2 (M+4+Na)$^+$, 685.2 (M+6+Na)$^+$, 695.2 (M+K)$^+$, 697.2 (M+2+K)$^+$, 699.2 (M+4+K)$^+$; $^1$H NMR (DMSO-d$_6$) δ10.08 (1 H, s, PAB-NH), 9.37 (1 H, s, C=NH), 8.10 (1 H, d, J=7.8 Hz, amide NH), 7.60 (2 H, d, J=8.4 Hz, PAB-CHx2), 7.21–7.38 (8 H, m, aromatic), 5.96 (1 H, t, J=5.1 Hz, cit-NH), 5.40 (2 H, s, cit-NH$_2$), 5.21 (2 H, s, PAB-CH$_2$), 5.02 (2 H, s, Cbz-CH$_2$), 4.40 (1 H, dd, J=13.2, 7.8 Hz, val-CH), 3.90 (1 H, t, J=8.4 Hz, cit-CH), 2.85–3.15 (2 H, m, cit-CH$_2$), 1.90–2.05 (1 H, m, val-CH), 1.28–1.74 (4 H, m, cit-CH$_2$), 0.86 (3 H, d, J=6.6 Hz, val-CH$_3$), 0.82 (3 H, d, J=6.9 Hz, val-CH$_3$). Anal. ($C_{28}H_{35}Cl_3N_6O_6 \cdot 0.2H_2O$, $0.4Et_3N$) C, H, N, Cl.

Example 3

(1S,2R)-N-ACETYL-NOREPHEDRINE (4)

(1S,2R)-(+)-norephedrine (5.0 g, 32.4 mmol) was partially suspended in water (65 mL, 0.5 M). Acetic anhydride (6.2 mL, 64.8 mmol, 2.0 eq) was added, and the resulting yellow solution was stirred for 1 h. EtOAc was added, the layers were separated, and the aqueous layer was further washed with EtOAc (2×). The combined extracts were washed with brine and dried (MgSO$_4$). Filtration, followed by removal of solvent led to a yellow oil that slowly formed yellow crystals. The crude product was purified by chromatography on SiO$_2$ (1:1 CH$_2$Cl$_2$-EtOAc) and the combined fractions were concentrated to a clear oil that solidified. Recrystallization from EtOAc-hexanes gave a white cotton-like solid as the desired product (4.95 g, 79%): mp 123° C.; R$_f$ 0.14 (1:1 CH$_2$Cl$_2$-EtOAc); UV λ$_{max}$ 215, 256 nm; $^1$H NMR (CDCl$_3$) δ7.28–7.39 (5 H, m, aromatic), 5.59 (1 H, br d, J=8.4 Hz, NH), 4.87 (1 H, d, J=3.6 Hz, H-1), 4.34 (1 H, dp, J=3.0, 6.9 Hz, H-2),3.48 (1 H, br, s, OH), 2.01 (3 H, s, Ac), 1.02 (3 H, d, J=6.9 Hz, H-3). Anal. (C$_{11}$H$_{15}$NO$_2$) C, H, N.

Example 4

Cbz-val-cit-PAB-O-(N-Ac)-Nor (5)

The trichloroacetamidate 3 (1 eq) and alcohol 4 (1 eq) were suspended in anhydrous CH$_2$Cl$_2$ and cooled to 0° C. Dropwise addition of trifluoromethanesulfonic acid (0.5 eq) gave an immediate gummy precipitate. TLC analysis (9:1 CH$_2$Cl$_2$-MeOH) showed a product (R$_f$ 0.28) and some decomposition of 3 to Cbz-val-cit-PAB-OH 1 (R$_f$ 0.14). The contents were evaporated to a yellow solid and purified by chromatography on SiO$_2$ (eluent gradient 100% CH$_2$Cl$_2$ to 9:1 CH$_2$Cl$_2$-MeOH). The desired ether (5) was isolated as an off-white solid after triturating with diethyl ether: R$_f$ 0.28 (9:1 CH$_2$Cl$_2$-MeOH); UV λ$_{max}$ 215, 256 nm; LRMS (ESI$^+$) m/z 688.4 (M+H)$^+$, 711.4 (M+Na)$^+$; $^1$H NMR (DMSO-d$_6$) δ10.02 (1 H, s, PAB-NH), 8.10 (1 H, d, J=7.2 Hz, amide NH), 7.81 (1 H, d, J=9.0 Hz, amide NH), 7.56 (2 H, d, J=8.7 Hz, PAB-CHx2), 7.21–7.39 (12 H, m, aromatic), 5.98 (1 H, t, J=5.1 Hz, cit-NH), 5.41 (2 H, s, cit-NH$_2$), 5.03 (2 H, s, Cbz-CH$_2$), 4.06–4.45 (4 H, m, val-CH, Nor-CH, PAB-CH$_2$), 3.84–3.94 (2 H, m, cit-CH, Nor-CH), 2.85–3.15 (2 H, m, cit-CH$_2$), 1.87–2.04 (1 H, m, val-CH), 1.67 (3 H, s, Nor-Ac), 1.28–1.75 (4 H, m, cit-CH$_2$'s), 0.98 (3 H, d, J=6.6 Hz, Nor-CH$_3$), 0.86 (3 H, d, J=6.6 Hz, val-CH$_3$), 0.82 (3 H, d, J=6.9 Hz, val-CH$_3$).

Example 5

Cbz-val-cit-PAB-O-etoposide (6)

Following the Mitsunobu procedure described above, the pure fractions from chromatography on SiO$_2$ gave the ether as a white solid (64%); R$_f$ 0.29 (9:1 CH$_2$Cl$_2$-MeOH); UV λ$_{max}$ 215, 250, 290 nm; LRMS (ESI$^+$) m/z 1084.6 (M+H)$^+$, 1106.6 (M+Na)$^+$, 1122.6 (M+K)$^+$; $^1$H NMR (DMSO-d$_6$) δ10.01 (1 H, s, PAB-NH), 8.08 (1 H, d, J=7.2 Hz, amide NH), 7.57 (2 H, d, J=8.1 Hz, PAB-CHx2), 7.29–7.40 (7 H, m, aromatic), 7.00 (2 H, s, etop. aromatic), 6.53 (1 H, s, etop. aromatic), 6.23 (2 H, s, etop. aromatic), 6.01 (1 H, d, J=3.3 Hz, etop-CH$_2$), 5.96 (1 H, t, J=5.1 Hz, cit-NH), 5.40 (2 H, s, cit-NH$_2$), 5.24 (1 H, s, etop-OH), 5.22 (1 H, s, etop-OH), 5.02 (2 H, s, Cbz-CH$_2$), 4.92 (1 H, d, J=3.0 Hz, etop-CH), 4.74 (2 H, s, PAB-CH$_2$), 4.70 (1 H, dd, J=9.9, 4.8 Hz, etop-CH), 4.56 (1 H, d, J=7.8 Hz, etop-CH), 4.54 (1 H, d, J=5.1 Hz, etop-CH), 4.36–4.44 (1 H, m, val-CH), 4.25 (2 H, dd, J=9.0 Hz, etop-CHx2), 4.06 (1 H, dd, J=11.1, 4.8 Hz, etop-CH), 3.90 (1 H, t, J=6.9 Hz, cit-CH), 3.62 (6 H, s, etop-OCH$_3$x2), 3.49 (1 H, t, J=9.6 Hz, etop-CH), 2.81–3.30 (9 H, m, etop-CHx7, cit-NCH$_2$), 1.88–2.05 (1 H, m, val-CH), 1.30–1.74 (4 H, m, cit-CH$_2$'s), 1.22 (3 H, d, J=4.8 Hz, etop-CH$_3$), 0.86 (3 H, d, J=6.6 Hz, val-CH$_3$), 0.82 (3 H, d, J=6.9 Hz, val-CH$_3$). Anal. (C$_{55}$H$_{65}$N$_5$O$_{18}$·2H$_2$O) C, H, N.

Example 6

Cbz-val-cit-PAB-3'-O-combretastatin A-4 (7)

Using the Mitsunobu reaction conditions described above, the compound was isolated as an amorphous solid after trituration ether. R$_f$ 0.42 (9:1 CH$_2$Cl$_2$-MeOH); mp 169–172 (dec); UV λ$_{max}$ 215, 248, 300 nm; LRMS (ESI$^+$) m/z 812.4 (M+H)$^+$, 834.4 (M+Na)$^+$, 850.4 (M+K)$^+$; $^1$H NMR (DMSO-d$_6$) δ10.06 (1 H, s, PAB-NH), 8.11 (1 H, d, J=7.2 Hz, amide NH), 7.57 (2 H, d, J=8.4 Hz, PAB-CHx2), 7.24–7.45 (6 H, m, aromatic), 7.21 (2 H, d, J=8.4 Hz, PAB-CHx2), 6.82–6.98 (2 H, m, CSA4-H-5', 6'), 6.56 (2 H, s, CSA4-H-2), 6.48 (2 H, d, J=12.3 Hz, CSA4-cis-CH), 6.44 (2 H, d, J=12.3 Hz, CSA4-cis-CH), 5.97 (1 H, t, J=5.1 Hz, cit-NH), 5.41 (2 H, s, cit-NH$_2$), 5.03 (2 H, s, Cbz-CH$_2$), 4.76 (2 H, s, PAB-CH$_2$), 4.36–4.45 (1 H, m, val-CH), 3.92 (1 H, t, J=7.2 Hz, cit-CH), 3.82 (3 H, s, CSA4–3'-OCH$_3$), 3.61 (9 H, s, CSA4–3,4,5-OCH$_3$), 2.88–3.07 (2 H, m, cit-NCH$_2$), 190-2.03 (1 H, m, val-CH), 1.28–1.78 (4 H, m, cit-CH$_2$'s), 0.86 (3 H, d, J=6.6 Hz, val-CH$_3$), 0.82 (3 H, d, J=6.9 Hz, val-CH$_3$). Anal. (C$_{44}$H$_{53}$N$_5$O$_{10}$·H$_2$O) C, H, N.

Example 7

(1S,2R)-N-Acetyl-O-(4-nitrophenyloxycarbonyl) norephedrine (8)

Compound 4 (1.0 g, 5.17 mmol, 1.0 eq) and p-nitrophenylchloroformate (1.61 g, 7.76 mmol, 1.5 eq) were dissolved in anhydrous THF (12 mL, 0.5 M) while under N$_2$. Dry pyridine (0.63 mL, 7.76 mmol, 1.0 eq) was added via syringe over a 3 min period. The resulting turbid mixture contained no starting material after 15 min according to TLC (1:1 CH$_2$Cl$_2$-EtOAc). Solids were filtered off and washed with THF. The filtrate was concentrated to a yellow oil that was purified by chromatography on SiO$_2$ (1:1 hexanes-EtOAc). The desired product 8 was an off-white solid (1.43 g, 78%) that was stored in the dark at <0° C.: R$_f$ 0.16 (1:1 hexanes-EtOAc); UV λ$_{max}$ 215, 270 nm; $^1$H NMR (CDCl$_3$) δ8.24 (2 H, d, J=9.3 Hz, Pnp-CHx2), 7.38 (2 H, d, J=9.0 Hz, Pnp-CHx2), 7.32–7.44 (5 H, m, aromatic), 5.78 (1 H, d, J=3.3 Hz, H-1), 5.42 (1 H, br d, J=8.4 Hz, NH), 4.61 (1 H, dp, J=3.3, 7.2 Hz, H-2), 2.00 (3 H, s, Ac), 1.11 (3 H, d, J=7.2 Hz, H-3).

Example 8

3'-O-(4-Nitrophenyloxycarbonyl)combretastatin A-4 (9)

Using the same procedure as described above, combretastatin A-4 (120 mg, 0.38 mmol) was converted to the 4-nitrophenyl carbonate in quantitative yield (183 mg) and isolated as a yellow oil: R$_f$ 0.47 (3:2 hexanes-EtOAc); $^1$H NMR (CHCl$_3$) δ8.30 (2 H, d, J=9.3 Hz, Pnp-CHx2), 7.45 (2 H, d, J=9.3 Hz, Pnp-CHx2), 7.18 (2 H, d, J=1.5 Hz, H-2'), 6.88-6.94 (2 H, m, H-5',6'), 6.51 (1 H, d, J=12.0 Hz, cis-CH), 6.49 (2 H, s, H-2), 6.48 (1 H, d, J=12.0 Hz, cis-CH), 3.89 (3 H, s, 3'-OCH$_3$), 3.84 (3 H, s, 4-OCH$_3$), 3.70 (3 H, s, 3,5-OCH$_3$).

Example 9

Cbz-val-cit-PAB-OCO-(1S,2R)-(N-acetyl)norephedrine (10)

The activated carbonate 8 (90 mg, 0.25 mmol) and Cbz-val-cit-PAB-OH 1 (130 mg, 0.25 mmol) were suspended in dry $CH_2Cl_2$ (8 mL), followed by the addition of DMAP (34 mg, 0.28 mmol, 1.1 eq). The reaction was stopped after 26 h by the addition of EtOAc and 10% citric acid. The layers were separated and the organic phase was further washed with water and brine. A precipitate formed that was filtered and added to the separated EtOAc layer and concentrated. The resulting yellow solid was subjected to chromatography on $SiO_2$ (gradient eluent 95:5 to 9:1 $CH_2Cl_2$-MeOH). The desired product eluted first and was concentrated to a white flaky solid (35 mg, 19%) while Cbz-val-cit-PAB-OH (1) was recovered as the second eluate: $R_f$ 0.17 (9:1 $CH_2Cl_2$-MeOH); UV $\lambda_{max}$ 215, 256 nm; LRMS (ESI$^+$) m/z 792.5 (M+H)$^+$, 814.5 (M+Na)$^+$, 830.4 (M+K)$^+$; $^1$H NMR (DMSO-d$_6$) δ10.08 (1 H, s, PAB-NH), 8.10 (1 H, d, J=7.2 Hz, amide NH), 8.00 (1 H, d, J=7.8 Hz, amide NH), 7.59 (2 H, d, J=8.7 Hz, PAB-CHx2), 7.26–7.39 (10 H, m, aromatic), 7.24 (2 H, d, J=8.7 Hz, PAB-CHx2), 5.96 (1 H, t, J=5.1 Hz, cit-NH), 5.61 (1 H, d, J=4.2 Hz, Nor-CH), 5.40 (2 H, s, cit-NH$_2$), 5.07 (2 H, s, Cbz-CH$_2$), 5.03 (2 H, s, PAB-CH$_2$), 4.40 (1 H, dd, J=13.2, 7.8 Hz, val-CH), 4.03–4.14 (1 H, m, Nor-CH), 3.92 (1 H, t, J=7.8 Hz, cit-CH), 2.85–3.06 (2 H, m, cit-CH$_2$), 1.90–2.02 (1 H, m, val-CH), 1.74 (3 H, s, Nor-Ac), 1.28–1.75 (4 H, m, cit-CH$_2$'s), 0.96 (3 H, d, J=6.9 Hz, Nor-CH$_3$), 0.87 (3 H, d, J=6.9 Hz, val-CH$_3$), 0.83 (3 H, d, J=7.2 Hz, val-CH$_3$). Anal. ($C_{38}H_{48}N_6O_9 \cdot 1/2H_2O$) C, H, N.

Example 10

C$_{BZ}$-$_{VAL}$-$_{CIT}$-PAB-OCO-$_{COMBRETASTATIN}$ A-4 (11)

Activated combretastatin A-4 9 (120 mg, 0.25 mmol) and Cbz-val-cit-PAB-OH 1 (130 mg, 0.25 mmol) were suspended in dry $CH_2Cl_2$/pyridine (3 mL each) followed by the addition of DMAP (34 mg, 0.28 mmol, 1.1 eq). The reaction was sonicated for 2 h followed by stirring for 20 h. Evaporation of the reaction mixture followed by purification by chromatography on $SiO_2$ (gradient eluent 100% $CH_2Cl_2$ to 9:1 $CH_2Cl_2$-MeOH), and concentration of the appropriate fractions resulted in a yellow oil that was precipitated from $CH_2Cl_2$ (1 mL) through the addition of ether. This led to a yellow solid (83 mg, 38%): $R_f$ 0.47 (9:1 $CH_2Cl_2$-MeOH); mp 155–158 (dec); UV $\lambda_{max}$ 215, 245, 285 nm; LRMS (ESI$^+$) m/z 856.5 (M+H)$^+$, 878.5 (M+Na)$^+$, 894.5 (M+K)$^+$; $^1$H NMR (DMSO-d$_6$) δ10.10 (1 H, s, PAB-NH), 8.11 (1 H, d, J=7.8 Hz, amide NH), 7.62 (2 H, d, J=8.1 Hz, PAB-CHx2), 7.25–7.40 (8 H, m, aromatic), 7.15 (1 H, dd, J=8.7, 1.8 Hz, CSA4-H-6'), 7.07 (1 H, d, J=8.1 Hz, CSA4-H-5'), 7.06 (1 H, d, J=2.4 Hz, CSA4-H-2'), 6.51 (2 H, s, CSA4-H-2), 6.48 (2 H, s, CSA4-CH=CH), 5.97 (1 H, t, J=5.1 Hz, cit-NH), 5.42 (2 H, s, cit-NH$_2$), 5.14 (2H, s, Cbz-CH$_2$), 5.02 (2 H, s, PAB-CH$_2$), 4.40 (1 H, dd, J=12.9, 8.1 Hz, val-CH), 3.92 (1 H, t, J=7.2 Hz, cit-CH), 3.73 (3 H, s, CSA4-3'-OCH$_3$), 3.61 (3 H, s, CSA4-4-OCH$_3$), 3.58 (6 H, s, CSA4-3,5-OCH$_3$), 2.88–3.07 (2 H, m, cit-NCH$_2$), 1.88–2.04 (1 H, m, val-CH), 1.28–1.178 (4 H, m, cit-CH$_2$'s), 0.86 (3 H, d, J=6.9 Hz, val-CH$_3$), 0.82 (3 H, d, J=6.6 Hz, val-CH$_3$). Anal. ($C_{45}H_{53}N_5O_{12} \cdot H_2O$) C, H, N.

Example 11

General Procedure for Cathepsin B Assays

Bovine spleen cathepsin B (Sigma-Aldrich), dissolved in phosphate buffered saline (pH 7.2, 1 mg/mL final concentration), was activated as previously described (Bajkowski, A. S.; Frankfater, A. Specific Spectrophotometric Assays for Cathepsin B. *Anal. Biochem.* 1975, 68, 119–127). A 1.0 mM stock solution of the peptide substrate in DMSO was added to acetate buffer (25 mM) containing 1 mM EDTA (pH 5.1) to give a final concentration of 0.08–0.14 mM, and to this was added the activated enzyme (12–15 μg/mL). In the case of the naphthol ether 2, a 5.0 mM solution in MeOH was diluted to a final concentration of 0.22 mM. Periodically, aliquots were taken, quenched with an equal volume of MeCN, centrifuged, and 100 μL injections analyzed by HPLC (4.6 mm×15 cm C$_{18}$ column) with detection between 210 and 400 nm. The mobile phase consisted of (A) 5 mM sodium phosphate (pH 7) and (B) either MeOH (for compounds 2, 7, and 11) or MeCN (for compounds 5, 6, and 10). The gradient elution was 90% to 10% A over 10 min, followed by 5 min at 10% A, and the flow rate was 1.0 mL/min. The disappearance of substrate and the appearances of released alcohol and Cbz-val-cit were recorded. Cathepsin B hydrolysis rates were calculated according to the disappearance of substrate (Table 1).

TABLE 1

| Compound | Stability[a] | | | Specific activity of cathepsin B[b] |
|---|---|---|---|---|
| | pH 5.1 | pH 7.2 | Human serum | |
| 2 | 0% loss, 7 days | 0% loss, 7 days | 0% loss, 7 days | 350 nmol/min/mg |
| 5 | 0% loss 7 d | 0% loss 7 d | 0% loss 7 d | 145 nmol/min/mg[c] |
| 6 | 0% loss, 7 days | 0% loss, 7 days | t½48 hoursd[d] | 160 nmol/min/mg |
| 7 | 0% loss, 7 days | 0% loss, 7 days | 0% loss, 7 days | 61 nmol/min/mg |
| 10 | t½ 104 hours | t½ 79 hours | t½ 9 days | 150 nmol/min/mg |
| 11 | t½ 62 hours | t½ 55 hours | t½ 45 hours | 32 nmol/min/mg | a. measured as the loss of starting material and the appearance of the released alcohol at 37° C. in phosphate buffered saline at pH 7.2, acetate buffer at pH 5.1, or in pooled serum.
b. measured as the loss of starting material at 37° C. in pH 5.1 acetate buffer.
c. measured as the loss of starting material, which correlated to the appearance of Z-val-cit-COOH. HPLC analysis indicated that N-acetylnorephedrine
d. Etoposide (VIIIa) and the etoposide moiety of 6 were unstable in serum. There was no apparent breakdown of the peptide-linker in 6. No Cbz-val-cit-COOH, 1, or VIIIa were detected.

General Procedure for All Stability Studies

Solutions of the substrates (0.08–0.14 mM in DMSO, and 0.22 mM in MeOH for 2) were diluted 10–20-fold in PBS, acetate buffer (25 mM, pH 5.1), or pooled human serum, and incubation was carried out at 37° C. For the serum studies, equal volumes of MeCN were added and the samples were centrifuged prior to HPLC analysis. The other samples were injected directly into the HPLC.

In Vitro Cytotoxicity Assays

L2987 human lung adenocarcinoma cells were obtained as previously described (Svensson, H. P.; Vrudhula, V. M.; Emsweiler, J. E.; MacMaster, J. F.; Cosand, W. L.; Senter, P. D.; Wallace, P. M. In Vitro and In Vivo Activities of a Doxorubicin Prodrug in Combination with Monoclonal Antibody β-Lactamase Conjugates. *Cancer Res.* 1995, 55, 2357–2365). WM266/4 and IGR-39 human melanoma cells were obtained from ATCC (Manassas, Va.) and DSMZ (Braunschweig, Germany), respectively. L2987 and WM266/4 cells were grown in Roswell Park Memorial Institute (RPMI) medium containing 10% fetal bovine serum and 10 U/mL penicillin G and 10 μg/mL streptomycin sulfate. Dulbecco's modified Eagle's medium was used in place of RPMI for the IGR-39 cells. The cells (2,500 cells in 0.1 mL medium) were plated into 96-well plates, and after 24 h at 37° C., various concentrations of the drugs in medium (50 μL) were added in triplicate. Incubation was continued for an additional 24 h, the cultures were washed, and fresh medium (0.15 mL) was added. After 48 h at 37° C., [$^3$H] thymidine (25 μL, 0.5 μCi/well) was added, and the cultures were frozen and harvested 4 h later. Incorporation of label was measured using a β-counter.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A compound of the formula:

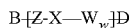

wherein:

D is a drug moiety;

B is a blocking group;

Z is an amino acid or a peptide residue;

X is an aminobenzyl ether self-immolative group;

W is an optional second self-immolative group;

w is an integer of 0 or 1;

wherein X—W forms an aminobenzyl ether when w is 1, and X-D forms an aminobenzyl ether when w is 0.

2. A compound of claim 1, represented by the following formula:

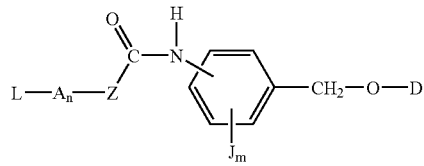

wherein:

—O-D is a portion of a drug, where the drug has the formula HO-D;

J is a substituent group, and m is 0, 1, 2, 3 or 4;

---

SEQUENCE LISTING

<160> NUMBER OF SEQ ID NOS: 2

<210> SEQ ID NO 1
<211> LENGTH: 4
<212> TYPE: PRT
<213> ORGANISM: Artificial Sequence
<220> FEATURE:
<223> OTHER INFORMATION: peptide group to illustrate the conjugates of
      the present invention

<400> SEQUENCE: 1

Gly Phe Leu Gly
 1

<210> SEQ ID NO 2
<211> LENGTH: 4
<212> TYPE: PRT
<213> ORGANISM: Artificial Sequence
<220> FEATURE:
<223> OTHER INFORMATION: peptide group to illustrate the conjugates of
      the present invention

<400> SEQUENCE: 2

Ala Leu Ala Leu
 1

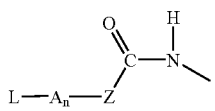

is situated at an ortho- or para-position with respect to the —CH$_2$— group;

Z-C(=O) is an amino acid or a peptide;

B is a hydrogen or a blocking group selected from a D-amino acid, and an N-terminus protecting group; wherein —CH$_2$—O-D forms an ether linkage.

3. A compound of claim 1, represented by the following formula:

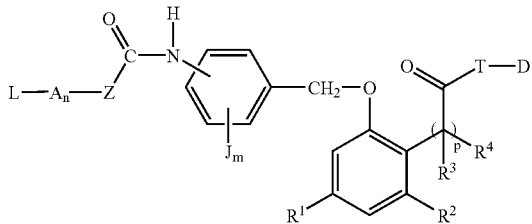

wherein:

T-D is a portion of a drug, where the drug has the formula HT-D;

T is O, S, NH, or N(lower alkyl);

J is a substituent group, and m is 0, 1, 2, 3 or 4;

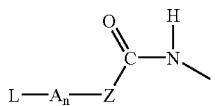

is situated at an ortho- or para-position with respect to the —CH$_2$— group;

Z-C(=O) is an amino acid or a peptide;

p is 1 or 2; and

B is a hydrogen or a blocking group selected from a D-amino acid, and an N-terminus protecting group.

4. A compound of claim 2 wherein the O of —O-D is bonded to a carbon that forms an aromatic ring of D.

5. A compound of claim 4 wherein the drug is 1,2,9,9a-tetra-hydro-cyclo-propa[c]benz[e]indol-4-one (CBI) conjugated to a minor groove binder.

6. A compound of claim 4 wherein the drug is cyclopropapyrroloindole (CPI) conjugated to a minor groove binder.

7. A compound of claim 4 wherein the drug is 1,2,9,9a-tetra-hydro-cyclo-propa[c]pyrido[3,2-e]indol-4-one (CPyI) conjugated to a minor groove binder.

8. A compound of claim 4 wherein the drug is selected from: ((S)—N-[2-[[1-(chloromethyl)-1,6-dihydro-5-hydroxy-8-methylbenzo[1,2-b: 4,3-b']dipyrrol-3(2-yl]carbonyl]-1H-indol-5-yl]-6-(diethylamino)-2-benzofurancarboxamide) (U-76,073); seco-adozelesin; bizelesin; 1,2,9,9a-tetra-hydro-cyclo-propa[c]benz[e]indol-4-one-trimethoxyindole (CBI-TMI); duocarmycin C2; duocarmycin B2; (Benzo(1,2-b:4,3-b')dipyrrole-3(2H)-carboxamide, 7-((1,6-dihydro-4-hydroxy-5-methoxy-7-((4,5,8, 8a-tetrahydro-7-methyl-4-oxocyclopropa(c)pyrrolo(3,2-e)indol-2(1H)-yl)carbonyl)benzo(1,2-b:4,3-b')dipyrrol-3(2H)-yl)carbonyl)-1,6-dihydro-4-hydroxy-5-methoxy-, (7bR)—) (seco-CC-1065); pancratistatin; carminomycin; streptonigrin; zorubicin; elliptinium acetate; mitoxantrone; daunorubicin; phenol mustard; doxorubicin; etoposide, combretastatin A-4, and 7-ethyl-10-hydroxycamptothecin (SN-38).

9. A compound of claim 4 wherein the O of —O-D is bonded to an aliphatic carbon of D.

10. A compound of claim 9 in which the drug is auristatin E.

11. A compound of claim 2 wherein the H of H—O-D has a pKa of 16 or less.

12. A compound of claim 3 wherein T is NH or N(lower alkyl).

13. A compound of claim 3 wherein T is O or S.

14. A compound of claim 12 wherein the drug is selected from 5-amino-1,2,9,9a-tetra-hydro-cyclopropa[c]benz[e]indol-4-one (CBI) conjugated to a minor groove binder; 5-amino-cyclopropapyrroloindole (CPI) conjugated to a minor groove binder, and 5-amino-1,2,9,9a-tetra-hydro-cyclopropa[c]pyrido[3,2-e]indol-4-one (CPyI) conjugated to a minor groove binder.

15. A compound of claim 12 wherein the drug is an amino containing drug moiety selected from the group consisting of mitomycin-C, mitomycin-A, daunorubicin, doxorubicin, N-(5,5-diacetoxypentyl)doxorubicin, aminopterin, actinomycin, bleomycin, 9-amino camptothecin, N$^8$-acetyl spermidine, 1-(2 chloroethyl)-1,2-dimethanesulfonyl hydrazide, tallysomycin, and derivatives thereof.

16. A compound of claim 13 wherein the drug is auristatin E.

17. A compound of claim 13 wherein the drug is a hydroxyl-containing moiety selected from the group consisting of: etoposide, camptothecin, taxol, esperamicin, 1,8-dihydroxy-bicyclo[7.3.1]trideca-4,9-diene-2,6-diyne-13-one, anguidine, doxorubicin, morpholino-doxorubicin, N-(5, 5-diacetoxypentyl)doxorubicin, vincristine, vinblastine and derivatives thereof.

18. A compound of claim 13 wherein the drug is a sulfhydryl-containing moiety selected from the group consisting of esperamicin, 6-mercaptopurine, and derivatives thereof.

19. A compound of claim 2 wherein m is 0.

20. A compound of claim 3 wherein m is 0.

21. A compound of claim 2 wherein m is 1 and the substituent is an electron-withdrawing group selected from F, Cl, Br, CN, CF$_3$, CONH$_2$, CHO, CO$_2$CH$_3$, COCH$_3$, NHCOCH$_3$, NO$_2$, and sulfonyl groups.

22. A compound of claim 2 wherein m is 1 and the substituent is an electron-withdrawing group selected from F, Cl, Br, CN, CF$_3$, CONH$_2$, CHO, CO$_2$CH$_3$, COCH$_3$, NHCOCH$_3$, NO$_2$, and sulfonyl groups.

23. A compound of claim 2 wherein Z is a dipeptide or a tripeptide.

24. A compound of claim 3 wherein Z is a dipeptide or a tripeptide.

25. A compound of claim 2 wherein Z is valine-citrulline.

26. A compound of claim 3 wherein Z is valine-citrulline.

27. A compound of claim 2 wherein Z is phenylalanine-lysine.

28. A compound of claim 3 wherein Z is phenylalanine-lysine.

29. A compound of claim 2 wherein

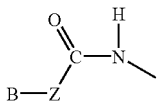

is situated at the para-position with respect to the —CH₂— group.

30. A compound of claim 3 wherein

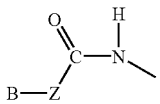

is situated at the para-position with respect to the —CH₂— group.

31. A compound of claim 2 wherein B is a carbobenzoxy protecting group.

32. A compound of claim 3 wherein B is a carbobenzoxy protecting group.

33. A pharmaceutical composition comprising a compound of claim 1 and a pharmaceutically acceptable carrier, diluent or excipient.

34. A pharmaceutical composition comprising a compound of claim 2 and a pharmaceutically acceptable carrier, diluent or excipient.

35. A pharmaceutical composition comprising a compound of claim 3 and a pharmaceutically acceptable carrier, diluent or excipient.

36. A compound of claim 1 wherein D is cytotoxic.

37. A compound of claim 2 wherein HO-D is cytotoxic.

38. A compound of claim 3 wherein HT-D is cytotoxic.

* * * * *

UNITED STATES PATENT AND TRADEMARK OFFICE
CERTIFICATE OF CORRECTION

PATENT NO.         : 7,091,186 B2                                  Page 1 of 3
APPLICATION NO. : 09/963103
DATED                  : August 15, 2006
INVENTOR(S)        : Peter D. Senter and Brian E. Toki It is certified that error appears in the above-identified patent and that said Letters Patent is hereby corrected as shown below:

IN THE CLAIMS

Claim 2 (Column 36, line 25):
delete the formula: " 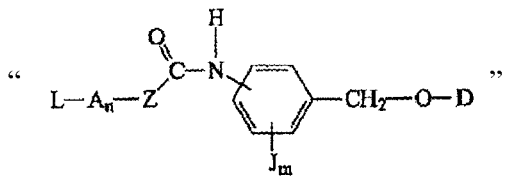 "

and insert the formula: -- 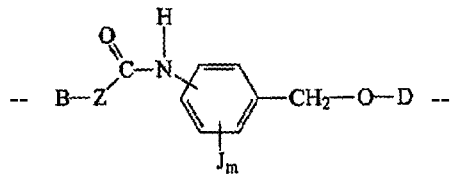 --

(Column 37, line 6):
delete the formula: " 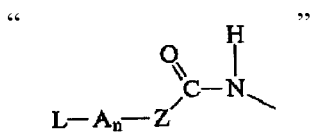 "

and insert the formula: -- 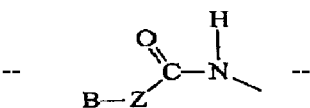 --

UNITED STATES PATENT AND TRADEMARK OFFICE
CERTIFICATE OF CORRECTION

PATENT NO. : 7,091,186 B2
APPLICATION NO. : 09/963103
DATED : August 15, 2006
INVENTOR(S) : Peter D. Senter and Brian E. Toki It is certified that error appears in the above-identified patent and that said Letters Patent is hereby corrected as shown below:

Claim 3 (Column 37, line 21):
delete the formula: " 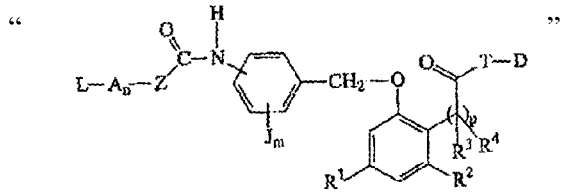 "

and insert the formula: -- 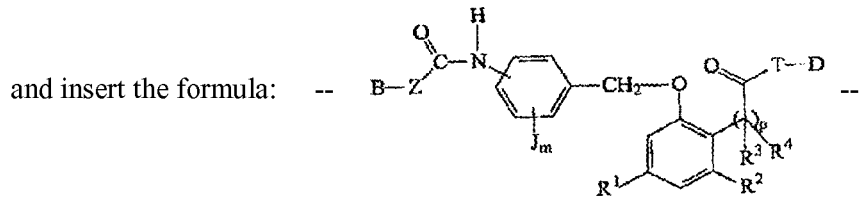 --

(Column 37, line 32): delete "0", and insert -- O --

UNITED STATES PATENT AND TRADEMARK OFFICE
CERTIFICATE OF CORRECTION

PATENT NO. : 7,091,186 B2
APPLICATION NO. : 09/963103
DATED : August 15, 2006
INVENTOR(S) : Peter D. Senter and Brian E. Toki It is certified that error appears in the above-identified patent and that said Letters Patent is hereby corrected as shown below:

(Column 37, line 38);
delete the formula: " 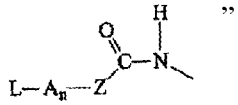 "

and insert the formula: -- 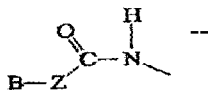 --

Claim 9 (Column 38, line 6): delete "4", and insert --2--

Claim 22 (Column 38, line 52): delete "2", and insert --3--

Signed and Sealed this

Twenty-sixth Day of August, 2008

JON W. DUDAS
*Director of the United States Patent and Trademark Office*